US010420817B2

(12) United States Patent
Hawthorne

(10) Patent No.: US 10,420,817 B2
(45) Date of Patent: *Sep. 24, 2019

(54) COMPOSITIONS AND METHODS FOR INHIBITING THE BIOLOGICAL ACTIVITY OF SOLUBLE BIOMOLECULES

(71) Applicant: NaNotics, LLC, Mill Valley, CA (US)

(72) Inventor: Louis Hawthorne, Mill Valley, CA (US)

(73) Assignee: NaNotics, LLC, Mill Valley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/909,820

(22) Filed: Mar. 1, 2018

(65) Prior Publication Data

US 2019/0038718 A1 Feb. 7, 2019

Related U.S. Application Data

(60) Continuation of application No. 15/450,769, filed on Mar. 6, 2017, now Pat. No. 9,907,831, which is a (Continued)

(51) Int. Cl.
*A61K 38/19* (2006.01)
*B82Y 30/00* (2011.01)
(Continued)

(52) U.S. Cl.
CPC .......... *A61K 38/191* (2013.01); *A61K 38/195* (2013.01); *A61K 38/2013* (2013.01);
(Continued)

(58) Field of Classification Search
CPC .............. A61K 38/191; A61K 47/6923; A61K 47/6739; A61K 47/642; B82Y 5/00; B82Y 30/00

See application file for complete search history.

(56) References Cited

U.S. PATENT DOCUMENTS 7,854,717 B1 12/2010 Lentz
7,932,311 B2 4/2011 Aymonier et al.
(Continued)

FOREIGN PATENT DOCUMENTS

DE 10144251 A1 3/2003
EP 1174129 A1 1/2002
(Continued)

OTHER PUBLICATIONS

"Magnetic Nanoparticle Biospleen Device for Sepsis Therapy," Wyss Institute for Biology Inspired Engineering at Harvard, http://www.nanowerk.com/nanotechnology-news/newsid=37354.php (pp. 1-8).
(Continued)

*Primary Examiner* — Carlos A Azpuru
(74) *Attorney, Agent, or Firm* — Foley Hoag LLP; David P. Halstead; Lucas P. Watkins

(57) ABSTRACT

The disclosure provides, among other things, compositions that bind to and inhibit the biological activity of soluble biomolecules, as well as pharmaceutical compositions thereof. Also provided herein are a number of applications (e.g., therapeutic applications) in which the compositions are useful.

25 Claims, 3 Drawing Sheets

Related U.S. Application Data division of application No. 14/873,847, filed on Oct. 2, 2015, now Pat. No. 9,623,081.

(60) Provisional application No. 62/198,541, filed on Jul. 29, 2015, provisional application No. 62/198,519, filed on Jul. 29, 2015, provisional application No. 62/059,628, filed on Oct. 3, 2014.

(51) Int. Cl.

| | |
|---|---|
| *B82Y 5/00* | (2011.01) |
| *A61K 38/20* | (2006.01) |
| *A61K 47/10* | (2017.01) |
| *A61K 47/60* | (2017.01) |
| *A61K 47/61* | (2017.01) |
| *A61K 47/62* | (2017.01) |
| *A61K 47/64* | (2017.01) |
| *A61K 47/69* | (2017.01) |

(52) U.S. Cl.
CPC .............. *A61K 47/10* (2013.01); *A61K 47/60* (2017.08); *A61K 47/61* (2017.08); *A61K 47/62* (2017.08); *A61K 47/642* (2017.08); *A61K 47/6923* (2017.08); *A61K 47/6929* (2017.08); *A61K 47/6937* (2017.08); *B82Y 5/00* (2013.01); *B82Y 30/00* (2013.01)

(56) References Cited

U.S. PATENT DOCUMENTS

| | | | |
|---|---|---|---|
| 8,133,490 | B2 | 3/2012 | Lentz |
| 8,586,096 | B2 | 11/2013 | Katti et al. |
| 8,685,538 | B2 | 4/2014 | Torchilin et al. |
| 8,926,994 | B2 | 1/2015 | Serda et al. |
| 9,623,081 | B2 | 4/2017 | Hawthorne |
| 9,907,831 | B2 * | 3/2018 | Hawthorne .............. B82Y 5/00 |
| 2004/0105821 | A1 | 6/2004 | Bernstein et al. |
| 2004/0166166 | A1 | 8/2004 | Matsunami et al. |
| 2004/0170626 | A1 | 9/2004 | Schuurman et al. |
| 2004/0265392 | A1 | 12/2004 | Tovar et al. |
| 2006/0199820 | A1 | 9/2006 | Bannen et al. |
| 2008/0075690 | A1 | 3/2008 | Howell |
| 2008/0277346 | A1 | 11/2008 | Kirkland et al. |
| 2012/0108787 | A1 | 5/2012 | Lue |
| 2012/0141797 | A1 | 6/2012 | Sherman et al. |
| 2013/0195972 | A1 | 8/2013 | Manku et al. |
| 2013/0196450 | A1 | 8/2013 | Van Hoonacker et al. |
| 2013/0337070 | A1 | 12/2013 | Brenneisen et al. |
| 2014/0010879 | A1 | 1/2014 | Shen et al. |
| 2014/0235803 | A1 | 8/2014 | Jiang et al. |
| 2014/0296836 | A1 | 10/2014 | Shen et al. |
| 2014/0341975 | A1 | 11/2014 | Livneh |
| 2015/0112842 | A1 | 4/2015 | Sieger et al. |
| 2015/0231233 | A1 | 8/2015 | Lentz |
| 2017/0038382 | A1 | 2/2017 | Hawthorne |
| 2017/0056327 | A1 | 3/2017 | Mi et al. |
| 2018/0256747 | A1 | 9/2018 | Hawthorne et al. |

FOREIGN PATENT DOCUMENTS

| | | | |
|---|---|---|---|
| EP | 1227843 | A2 | 8/2002 |
| EP | 1949915 | A2 | 7/2008 |
| WO | WO-2004/071641 | A2 | 8/2004 |
| WO | WO-2005/107802 | A2 | 11/2005 |
| WO | 2006086428 | A2 * | 8/2006 |
| WO | WO-2006/086428 | A2 | 8/2006 |
| WO | WO-2008/127515 | A1 | 10/2008 |
| WO | WO-2009/030492 | A2 | 3/2009 |
| WO | WO-2009061853 | A2 | 5/2009 |
| WO | WO-2010/042555 | A2 | 4/2010 |
| WO | WO-2012/163544 | A1 | 12/2012 |
| WO | WO-2013/029278 | A1 | 3/2013 |
| WO | WO-2013/179143 | A2 | 12/2013 |
| WO | WO-2014/041544 | A1 | 3/2014 |
| WO | 2014109842 | A2 * | 7/2014 |
| WO | WO-2014/109842 | A2 | 7/2014 |
| WO | WO-2015/112842 | A1 | 7/2015 |
| WO | WO-2016/054522 | A1 | 4/2016 |
| WO | WO-2017/004159 | A1 | 1/2017 |
| WO | 2017019949 | * | 2/2017 |
| WO | WO-2017/019949 | A1 | 2/2017 |
| WO | WO-2017/176762 | A1 | 10/2017 |
| WO | WO-2018/129188 | A1 | 7/2018 |
| WO | WO-2018/129207 | A1 | 7/2018 |

OTHER PUBLICATIONS

Aderka, et al., "Increased serum levels of soluble receptors for tumor necrosis factor in cancer patients," Cancer Res, 51(20): 5602-5607 (1991).

Cauda, et al., "Multiple core shell functionalized colloidal mesoporous silica nanoparticles," J American Chem Society, 131(32): 11361-11370 (2009).

Charych et al., "NKTR-214, an engineered cytokine with biased IL2 receptor binding, increased tumor exposure, and marked efficacy in mouse tumor models," Clin Cancer Res, 22(3):680-690 (2016).

Duffy et al., "The ADAMs: New Therapeutic Targets for Cancer?" Cancer Targeted Drug Delivery. Springer New York, 273-287 (2013).

Extended European Search Report issued by the European Patent Office in corresponding Application No. 15740254.6, dated Dec. 20, 2017.

Giai, Constanza et al. "Shedding of Tumor Necrosis Factor Receptor 1 Induced by Protein A Decreases Tumor Necrosis Factor Alpha Availability and Inflammation during Systemic *Staphylococcus aureus* Infection," Infection & Immunity, 81(11):4200 (2013).

Holtan, Shernan G. et al. "Cancer and Pregnancy: Parallels in Growth, Invasion, and Immune Modulation and Implications for Cancer Therapeutic Agents", Mayo Clinical Protocols, 84(11): 985-1000 (2008).

International Search Report and Written Opinion for International Application No. PCT/US2016/04474 dated Oct. 13, 2016.

International Search Report and Written Opinion for International Application No. PCT/US2017/025954 dated Sep. 8, 2017.

Li et al., "Engineered interleukin-2 antagonists for the inhibition of regulatory T cells," J Immunother, 32(9):887-894 (2009).

Li et al., "PEGylated recombinant human tumor necrosis factor alpha: preparation and anti-tumor potency, Acta Pharmacol Sin, 22(6):549-555 (2001).

Mullberg et al., "A Metalloprotease Inhibitor Blocks Shedding of the IL-6 Receptor and the p60 TNF Receptor," J Immunol, 155: 5198-5205 (1995).

Parker Annual Report 2014.

Partial Supplementary European Search Report issued by the European Patent Office in corresponding Application No. EP 15740254.6, dated Sep. 25, 2017.

Sheu et al., "A Novel Role of Metalloproteinase in Cancer-mediated Immunosuppression," Cancer Res, 61: 237-242 (2001).

Waldmann et al.,"Anti-Tac (daclizumab, Zenapax) in the treatment of leukemia, autoimmune diseases, and in the prevention of allograft rejection: a 25-year personal odyssey," J Clin Immunol, 27(1):1-18 (2007).

Yang et al., "The use of polyethylene glycol modified interleukin 2 (PEG IL 2) in the treatment of patients with metastatic renal cell carcinoma and melanoma," Cancer, 76(4):687-694 (1995).

Yousef, Hanadie et al. "Systemic Attenuation of the TGFβ Pathway by a Single Drug Simultaneously Rejuvenates Hippocampal Neurogenesis and Myogenesis in the same old Mammal," Oncotarget, 6(14):11959 (2015).

Douglas et al., "Self-assembly of DNA into nanoscale three-dimensional shapes," Nature, 459(7245):414-418 (2009).

Extended European Search Report for EP Application No. 16818651.8 dated Jan. 31, 2019.

Extended European Search Report received for EP Patent Application No. EP16831405.2, dated Feb. 5, 2019.

(56) References Cited

OTHER PUBLICATIONS

International Preliminary Report on Patentability for International Application No. PCT/US2017/025954 dated Oct. 9, 2018.
International Search Report and Written Opinion for International Application No. PCT/US2018/012386, dated Mar. 28, 2018.
International Search Report and Written Opinion for International Application No. PCT/US2018/012414, dated Mar. 28, 2018.

* cited by examiner

COMPOSITIONS AND METHODS FOR INHIBITING THE BIOLOGICAL ACTIVITY OF SOLUBLE BIOMOLECULES

PRIORITY

This patent application is a continuation of U.S. patent application Ser. No. 15/450,769, filed Mar. 6, 2017, now U.S. Pat. No. 9,907,831, which is a divisional of U.S. patent application Ser. No. 14/873,847, filed Oct. 2, 2015, now U.S. Pat. No. 9,623,081, which claims the benefit of and priority to U.S. Provisional Patent Application No. 62/059,628, filed Oct. 3, 2014, U.S. Provisional Patent Application No. 62/198,519, filed Jul. 29, 2015, and U.S. Provisional Patent Application No. 62/198,541, filed Jul. 29, 2015, each of which is hereby incorporated by reference in its entirety.

BACKGROUND

Dozens of anti-cancer therapies available clinically or under development involve stimulation of the immune system's ability either to recognize or destroy cancer, or both. Three of the most prominent are the anti-checkpoint inhibitors Yervoy (Ipilimumab) from Bristol-Myers Squibb, Keytruda (Pembrolizumab, formerly Lambrolizumab) from Merck, and the cell therapy known as adoptive cell transfer with tumor infiltrating lymphocytes (ACT/TIL) from Moffitt Cancer Center/National Cancer Institute. However, these and other approaches involve net up-regulation of a subject's immune system, inducing potentially serious symptoms akin to autoimmune disorders and/or other significant side effects.

There is a need in the art for more effective pharmacological approaches for addressing cancer, particularly metastatic cancer, without disturbing a subject's capacity for avoiding auto-immunity. Among other things, the present disclosure provides methods and compositions based on alternative approaches for harnessing a subject's own immune system against cancer, including dis-inhibiting the tumor microenvironment, i.e., weakening the tumor's defensive system, versus stimulating immune cells.

SUMMARY

The disclosure provides, among other things, compositions that bind to and inhibit the biological activity of soluble biomolecules, as well as pharmaceutical compositions thereof. Also provided herein are a number of applications in which the compositions are useful. For example, compositions described herein are useful for inhibiting proliferation, growth, and/or survival of a cell, such as a cancer cell. In another example, compositions described herein can be useful to bind to and neutralize toxins (e.g., zootoxins, bacterial toxins, and/or plant toxins), viruses, or other foreign compounds in the circulation of a subject.

"Polypeptide," "peptide," and "protein" are used interchangeably and mean any peptide-linked chain of amino acids, regardless of length or post-translational modification.

Unless otherwise defined, all technical and scientific terms used herein have the same meaning as commonly understood by one of ordinary skill in the art to which this disclosure pertains. Preferred methods and materials are described below, although methods and materials similar or equivalent to those described herein can also be used in the practice or testing of the presently disclosed methods and compositions. All publications, patent applications, patents, and other references mentioned herein are incorporated by reference in their entirety.

The disclosure contemplates all combinations of any of the foregoing aspects and embodiments, as well as combinations with any of the embodiments set forth in the detailed description and examples.

Figure 1:
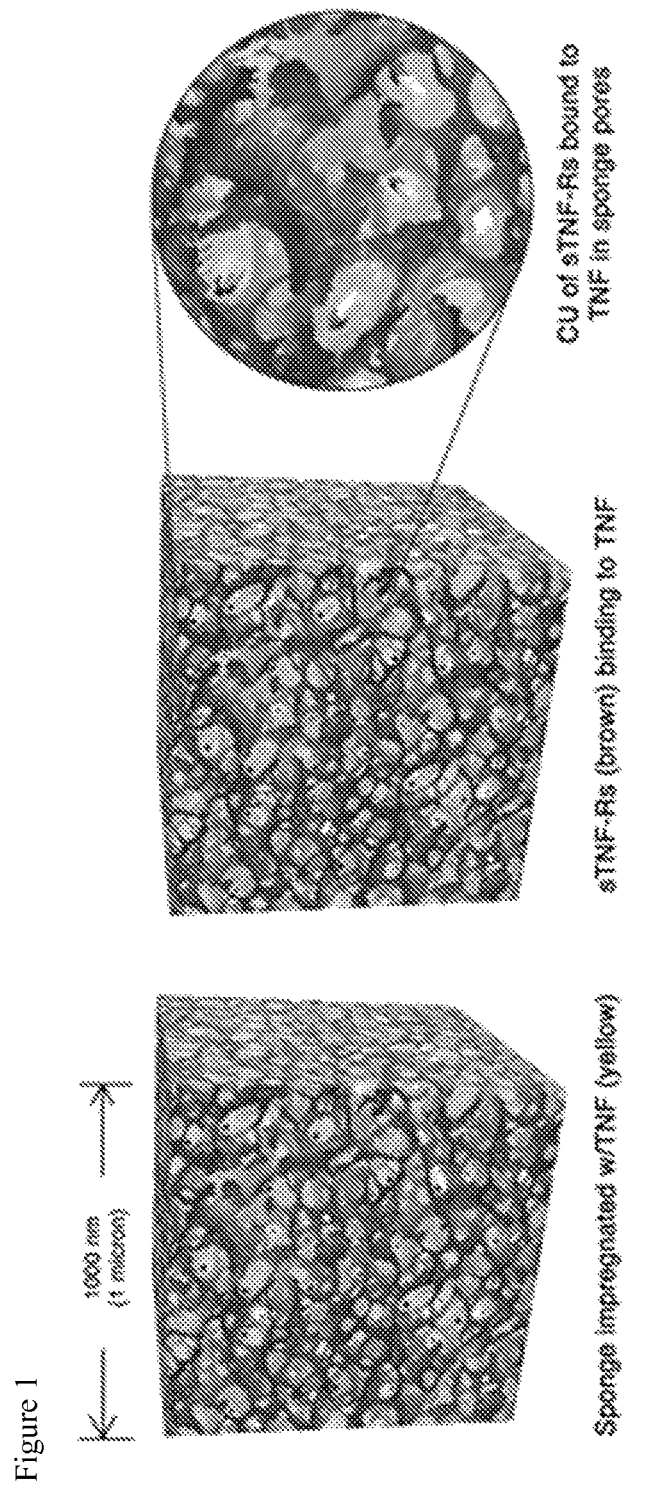
FIG. 1 depicts an exemplary embodiment of a particle that binds to soluble forms of TNF receptor (TNFR). The particle is one cubic micron. The inner surfaces of the particle contain immobilized TNF, which is capable of binding to soluble TNFR and sequestering (scavenging) it away from its natural ligands.

FIG. 2 depicts an exemplary embodiment of a particle that binds to soluble forms of TNF receptor (TNFR). The ring-shaped particle has a diameter of 175 nm. The inner surfaces of the particle contain immobilized TNF, which is capable of binding to soluble TNFR and sequestering (scavenging) it away from its natural ligands.

FIG. 3 depicts exemplary embodiments of particles that bind to soluble forms of TNF receptor (TNFR). The particle at the left of the figure is an octahedron with a core having a longest dimension of 100 to 150 nm. The particle at the right of the figure is an icosahedron with a core having a longest dimension of 200 to 300 nm. Each particle further comprises molecular protrusions pointing outward from the vertices of the core polyhedral structure. The protrusions serve as "cell repellers", which inhibit the interaction between the TNF bound to the particle and cell surface TNFR.

DETAILED DESCRIPTION

The disclosure features compositions and methods for sequestering a soluble biomolecule away from its natural environment, e.g., to thereby inhibit the biological activity of the soluble biomolecule. For example, the disclosure provides a particle, or a plurality of particles, having a surface comprising an agent (e.g., immobilized on a surface of the particle) that selectively binds to a soluble biomolecule. Once the soluble biomolecule is bound by the agent, it is sequestered by the particle such that the soluble biomolecule has a reduced ability (e.g., substantially reduced ability or no ability) to interact with other natural binding partners of the soluble biomolecule. Thus, the soluble biomolecule becomes inert.

I. Biomolecule

The soluble biomolecule is, generally, a first member of a specific binding pair. As used herein, a "binding partner", "specific binding partner", or a "member of a specific binding pair," generally comprises any member of a pair of binding members that bind to each other with substantial affinity and specificity. A pair of binding partners may bind to one another to the substantial exclusion of at least most or at least substantially all other components of a sample, and/or may have a dissociation constant of less than about $10^{-4}$, $10^{-5}$, $10^{-6}$, $10^{-7}$, or $10^{-8}$ M, among others. A pair of binding partners may "fit" together in a predefined manner that relies on a plurality of atomic interactions to cooperatively increase specificity and affinity. Binding partners may be derived from biological systems (e.g., receptor-ligand interactions), chemical interactions, and/or by molecular imprinting technology, among others. Exemplary corresponding pairs of binding partners, also termed specific binding pairs, are presented in Table 1, with the designations "first" and "second" being arbitrary and interchangeable.

The term "biomolecule" as used herein, refers to any molecule that may exert an effect on a living organism. In some embodiments, the biomolecule is an atom, such as lithium or lead (e.g., the biomolecule may be a metal cation). In some embodiments, the biomolecule is not an atom or metal ion. For example, the biomolecule may be a molecule, such as an organic compound or inorganic compound. In some embodiments, the biomolecule is a drug, such as warfarin. The biomolecule may be a psychoactive drug, such as diacetylmorphine. The biomolecule may be a poison, toxin, or venom. The biomolecule may be an allergen. The biomolecule may be a carcinogen. The biomolecule may be the agent of a chemical weapon, such as a nerve agent. The biomolecule may be a virus or viroid. The biomolecule may be a molecule that is endogenous to the organism, such as a hormone, cytokine, neurotransmitter, soluble extracellular receptor, antibody, or soluble matrix protein. The biomolecule may be a peptide, polypeptide, protein, nucleic acid, carbohydrate, or sugar. The biomolecule may comprise a peptide, polypeptide, protein, nucleic acid, carbohydrate, or sugar. The biomolecule may be a lipid, a steroid, or cholesterol.

The biomolecule may be a ligand of a cell surface receptor. The ligand may be a naturally-occurring ligand or a synthetic ligand. The ligand may be a native ligand of the receptor (e.g., a ligand that is produced by a subject in vivo) or a non-native ligand (e.g., a ligand that is introduced into the subject, such as a virus or drug). The biomolecule may be a ligand for a cytosolic receptor or a nuclear receptor.

TABLE 1

Examples of specific binding pairs.

| First Binding Partner | Second Binding Partner |
|---|---|
| Cell Surface Receptor (e.g., TNF receptor) | Natural Ligand (e.g., TNFα) |
| Viral Coat or Envelope Protein (e.g., HIV-1 gp120) | Corresponding Cellular Receptor (e.g., CD4) |
| Botulinum Toxin | Synaptotagmin II Cell Surface Receptor |
| Soluble Receptor (e.g., soluble TNFR or soluble IL-2 receptor) | Natural Ligand (e.g., TNFα or IL-2) |

As described above, tumor cells are known to protect themselves from host immune surveillance by shedding soluble forms of cytokine receptors, which soluble receptors bind to the cytokines produced by immune cells in the tumor microenvironment. For example, cancer cells shed soluble forms of TNF receptor and other cytokine receptors, such as IL-2 receptor and TRAIL receptor. These soluble receptors confer a growth advantage to cancer cells by relieving the cells of the pro-apoptotic effects of the TNFα, IL-2, and TRAIL. Karpatova et al. report the shedding of the 67 kD laminin receptor by human cancer cells, which may augment tumor invasion and metastasis ((1996) *J Cell Biochem* 60(2):226-234). Thus, the particles described herein can be engineered for scavenging soluble forms of cell surface receptor proteins, e.g., for use in the treatment of cancer.

Accordingly, in some embodiments, the cell surface receptor protein is expressed by a cancer cell and/or the cell surface receptor protein is a protein shed by the cancer cell as a soluble form of the cell surface receptor protein. In some embodiments, the cell surface receptor protein, when activated, induces apoptosis (e.g., a death receptor). In some embodiments, the cell surface receptor protein is a tumor necrosis factor receptor (TNFR) protein (e.g., TNFR-1 or TNFR-2). In some embodiments, the cell surface receptor protein is a Fas receptor protein. In some embodiments, the cell surface receptor protein is a TNF-related apoptosis-inducing ligand receptor (TRAILR) protein, 4-1BB receptor protein, CD30 protein, EDA receptor protein, HVEM protein, lymphotoxin beta receptor protein, DR3 protein, or TWEAK receptor protein. In some embodiments, the cell surface receptor protein is an interleukin receptor protein, e.g., an IL-2 receptor protein. It is understood that in such embodiments, the target soluble biomolecule can be a soluble form of the cell surface receptor, e.g., shed from a cancer cell.

A skilled artisan will also appreciate that the particles described herein are also useful for scavenging a wider variety of soluble biomolecules whose biological activity may be, e.g., undesirable. For example, the particles can be engineered to bind to components of viral capsids or envelopes to thereby sequester virus from the blood of a subject. The particles may be, in some embodiments, engineered to bind and sequester toxins (e.g., bacterial toxins, plant toxins, and zootoxins, such as one or more components of snake venom) in the circulation of a subject. In some embodiments, the particles can be engineered to bind to and sequester small molecules (e.g., illicit drugs or small molecular toxins) from the circulation of a subject. In such embodiments, the particles can be useful to remove toxins from the body, e.g., following a snake or insect bite. In some embodiments, the particles can be used for treating, preventing, delaying the onset, or reducing the severity of, anaphylactic shock in a subject (e.g., by scavenging the antigen giving rise to the anaphylactic immune response).

In some embodiments, the soluble biomolecule is a virus, e.g., a viral structural protein (such as a viral capsid or viral envelope protein) that is bound by the agent. In such embodiments, the particles are useful as anti-viral therapies, e.g., for a subject infected with a virus or at risk of being infected with a virus.

In some embodiments, the soluble biomolecule is a small molecule or macromolecule. In some embodiments, the longest dimension of the soluble biomolecule is no greater than 600 nm (e.g., less than 550, 500, 450, 400, 350, 300, 250, 200, 150, 100, 50, or 25 nm). The biomolecule may have a molecular radius of about 1 Å to about 1 μm, such as about 1 Å to about 100 nm, about 1 Å to about 20 nm, about 1 nm to about 1 μm, about 1 nm to about 100 nm, or about 1 nm to about 20 nm. The biomolecule may have a molecular weight of about 3 amu to about $10^7$ amu, such as about 100 amu to about $10^7$ amu, about 3 amu to about $10^6$ amu, about 3 amu to about $10^5$ amu, about 100 amu to about $10^6$ amu, or about 400 amu to about $10^6$ amu.

The terms "specific binding," "specifically binds," "selective binding", "selectively binds" and like grammatical terms, as used herein, refer to two molecules forming a complex that is relatively stable under physiologic conditions. Typically, binding is considered specific when the association constant ($k_a$) is higher than $10^6$ $M^{-1}$ $s^1$. Thus, a first member of a specific binding pair can specifically bind to the second member of the binding pair with a $k_a$ of at least (or greater than) $10^6$ (e.g., at least or greater than $10^7$, $10^8$, $10^9$, $10^{10}$, $10^{11}$, $10^{12}$, $10^{13}$, $10^{14}$, or $10^{15}$ or higher) $M^{-1}$ $s^{-1}$. In some embodiments, a selective interaction has a dissociation constant ($k_d$) of less than or equal to $10^{-3}$ (e.g., $8\times10^{-4}$, $5\times10^{-4}$, $2\times10^{-4}$, $10^{-4}$, or $10^{-5}$) $s^{-1}$.

In some embodiments, a selective interaction has a $K_D$ of less than $10^{-8}$, $10^{-9}$, $10^{-10}$, $10^{-11}$, or $10^{-12}$ M. The equilibrium constant $K_D$ is the ratio of the kinetic rate constants—$k_d/k_a$. In some embodiments, a selective interaction has a $K_D$ of less than $1 \times 10^{-9}$ M.

As used herein, the term "interaction", when referring to an interaction between two molecules, refers to the physical contact (e.g., binding) of the molecules with one another. Generally, such an interaction results in an activity (which produces a biological effect) of one or both of said molecules. To inhibit such an interaction results in the disruption of the activity of one or more molecules involved in the interaction.

As used herein, the term "inhibiting" and grammatical equivalents thereof refer to a decrease, limiting, and/or blocking of a particular action, function, or interaction. In one embodiment, the term refers to reducing the level of a given output or parameter to a quantity (e.g., the background level of the interaction between two members of a specific binding pair) which is at least 10%, 15%, 20%, 25%, 30%, 35%, 40%, 45%, 50%, 55%, 60%, 65%, 70%, 75%, 80%, 85%, 90%, 95%, 99% or less than the quantity in a corresponding control. A reduced level of a given output or parameter need not, although it may, mean an absolute absence of the output or parameter. The invention does not require, and is not limited to, methods that wholly eliminate the output or parameter. Substantial inhibition can be, e.g., at least 50 (e.g., 55, 60, 65, 70, 75, 80, 85, 90, or 95 or greater) % inhibition of an interaction between two biomolecules (e.g., the first and second members of a binding pair).

Methods for detecting an interaction or measuring the affinity of one biomolecule for another are known in the art. For example, the binding of two biomolecules can be detected and/or quantified using a variety of techniques such as, but not limited to, BioLayer Interferometry (BLI), Western blot, dot blot, surface plasmon resonance method (SPR), enzyme-linked immunosorbent assay (ELISA), AlphaScreen® or AlphaLISA® assays, or mass spectrometry based methods.

In some embodiments, binding can be assayed using any SPR-based assays known in the art for characterizing the kinetic parameters of the interaction of two biomolecules. Any SPR instrument commercially available including, but not limited to, BIAcore Instruments (Biacore AB; Uppsala, Sweden); lAsys instruments (Affinity Sensors; Franklin, Mass.); IBIS system (Windsor Scientific Limited; Berks, UK), SPR-CELLIA systems (Nippon Laser and Electronics Lab; Hokkaido, Japan), and SPR Detector Spreeta (Texas Instruments; Dallas, Tex.) can be used in the methods described herein. See, e.g., Mullett et al. (2000) *Methods* 22: 77-91; Dong et al. (2002) *Reviews in Mol Biotech* 82: 303-323; Fivash et al. (1998) *Curr Opin Biotechnol* 9: 97-101; and Rich et al. (2000) *Curr Opin Biotechnol* 11: 54-61.

In some embodiments, biomolecular interactions between two biomolecules can be assayed using BLI on an Octet (ForteBio Inc.). BLI is a label-free optical analytical technique that senses binding between a ligand that is immobilized on a biosensor tip and an analyte in solution by measuring the change in the thickness of the protein layer on the biosensor tip in real-time.

In some embodiments, AlphaScreen (PerkinElmer) assays can be used to characterize binding of two biomolecules. The acronym ALPHA stands for Amplified Luminescent Proximity Homogeneous Assay. AlphaScreen is a bead-based proximity assay that senses binding between molecules attached to donor and acceptor beads by measuring the signal produced by energy transfer between the donor and acceptor beads. (See e.g., Eglen et al. (2008) *Curr Chem Genomics* 1:2-10).

In some embodiments, AlphaLISA® (PerkinElmer) assays can be used to characterize binding of two biomolecules. AlphaLISA is modified from the AlphaScreen assay described above to include europium-containing acceptor beads and functions as an alternative to traditional ELISA assays. (See, e.g., Eglen et al. (2008) *Curr Chem Genomics* 1:2-10.)

A variety of immunoassay techniques, including competitive and non-competitive immunoassays, can be used. The term "immunoassay" encompasses techniques including, without limitation, flow cytometry, FACS, enzyme immunoassays (EIA), such as enzyme multiplied immunoassay technique (EMIT), enzyme-linked immunosorbent assay (ELISA), IgM antibody capture ELISA (MAC ELISA), and microparticle enzyme immunoassay (MEIA), furthermore capillary electrophoresis immunoassays (CEIA), radio-immunoassays (RIA), immunoradiometric assays (IRMA), fluorescence polarization immunoassays (FPIA), and chemiluminescence assays (CL). If desired, such immunoassays can be automated. Immunoassays can also be used in conjunction with laser induced fluorescence. Liposome immunoassays, such as flow-injection liposome immunoassays and liposome immunosensors, are also suitable for use in the present invention. In addition, nephelometry assays, in which, for example, the formation of biomolecular complexes results in increased light scatter that is converted to a peak rate signal as a function of the marker concentration, are suitable for use in the methods of the present invention. In a preferred embodiment of the present invention, the incubation products are detected by ELISA, RIA, fluoro immunoassay (FIA) or soluble particle immune assay (SPIA).

In some embodiments, binding of two biomolecules can be assayed using thermodenaturation methods involving differential scanning fluorimetry (DSF) and differential static light scattering (DSLS).

In some embodiments, binding of two biomolecules can be assayed using a mass spectrometry based method such as, but not limited to, an affinity selection coupled to mass spectrometry (AS-MS) platform. This is a label-free method where the protein and test compound are incubated, unbound molecules are washed away and protein-ligand complexes are analyzed by MS for ligand identification following a decomplexation step.

In some embodiments, binding of two biomolecules can be quantitated using, for example, detectably labeled proteins such as radiolabeled (e.g., $^{32}P$, $^{35}S$, $^{14}C$ or $^{3}H$), fluorescently labeled (e.g., FITC), or enzymatically labeled biomolecule, by immunoassay, or by chromatographic detection.

In some embodiments, the present invention contemplates the use of fluorescence polarization assays and fluorescence resonance energy transfer (FRET) assays in measuring, either directly or indirectly, the degree of interaction between two biomolecules.

II. Particles

As used herein, the term "particle" refers to a small mass that can comprise any material, such as alumina, metal (e.g., gold or platinum), glass, silica, latex, plastic, agarose, polyacrylamide, methacrylate or any polymeric material, and be of any size and shape. In some embodiments, the particle or particles comprise silicon. See, e.g., International Patent Application Publication Nos. WO 2013/011764, WO 2013/029278, and WO 2014/151381, and U.S. Patent Application Publication No. 2014/0271886, the disclosures of each of which are incorporated by reference in their entirety. In some embodiments, the particles can comprise or consist of starch (see, e.g., International Patent Application Publication No. WO 2010/084088).

Also featured herein are collections of particles. In some embodiments, the plurality of particles has a narrow or broad polydispersity. As used herein, "polydispersity" refers to the range of sizes of particles within a particular particle population. That is, an extremely polydisperse population might involve particles having a mean size of, say, 1 micron with individual particles ranging from 0.1 to 4 microns. In some embodiments, a "narrow polydispersity" is preferred. That is, given a particular mean particle size, it is presently preferred that individual particles in the population differ by no more than ±20%, preferably no more than ±15%, and most preferably at present no more than ±10% from the mean particle size. More specifically, a particle population preferably has a mean particle size of about 1 micron or less. Thus, if a mean particle size of 1 micron is selected, individual particles in the population would most preferably be within the range of from about 0.8 to about 1.2 microns. In some embodiments, the particle population has a mean particle size of about 0.3 to about 1 micron, e.g., about 0.4 to about 0.9, about 0.5 to about 0.9, about 0.4 to about 0.8, about 0.5 to about 0.7, about 0.3 to about 0.9, or about 0.3 to about 0.7 microns.

Figure 2:
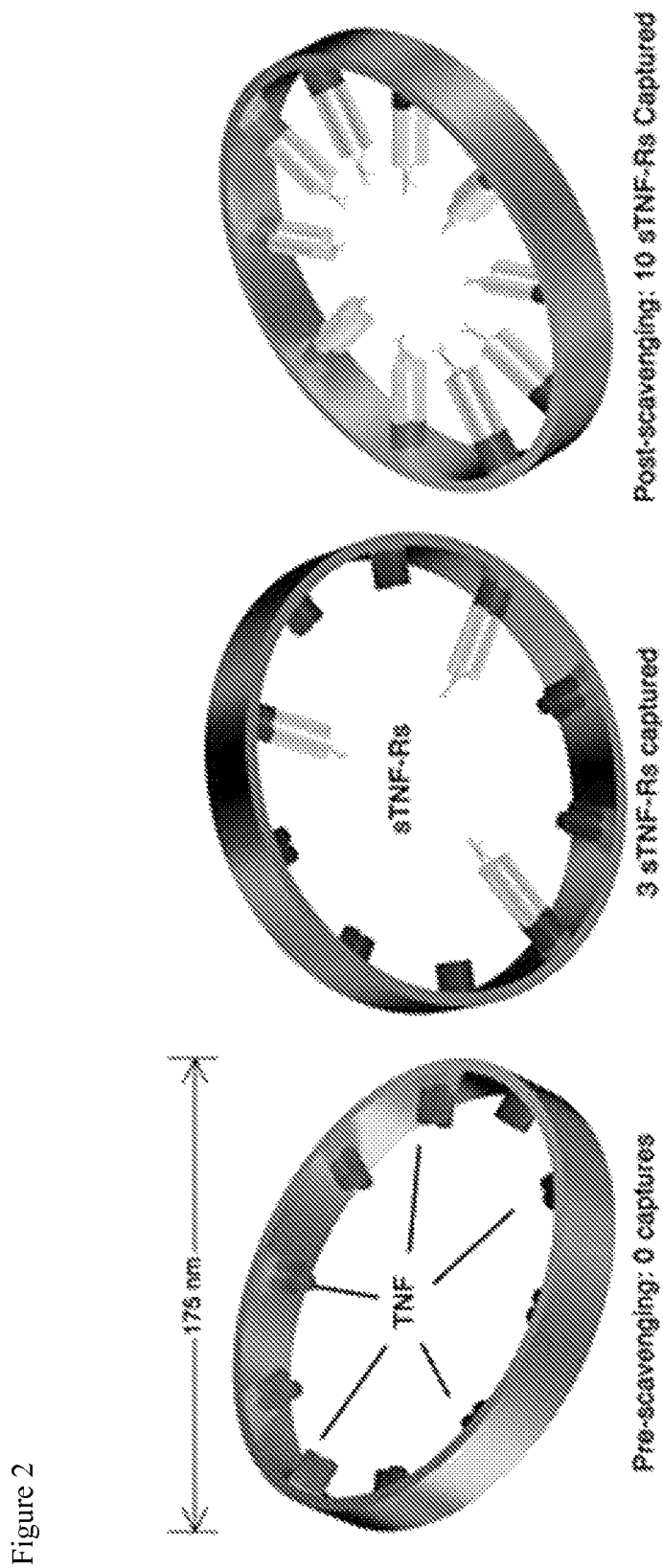
Figure 3:
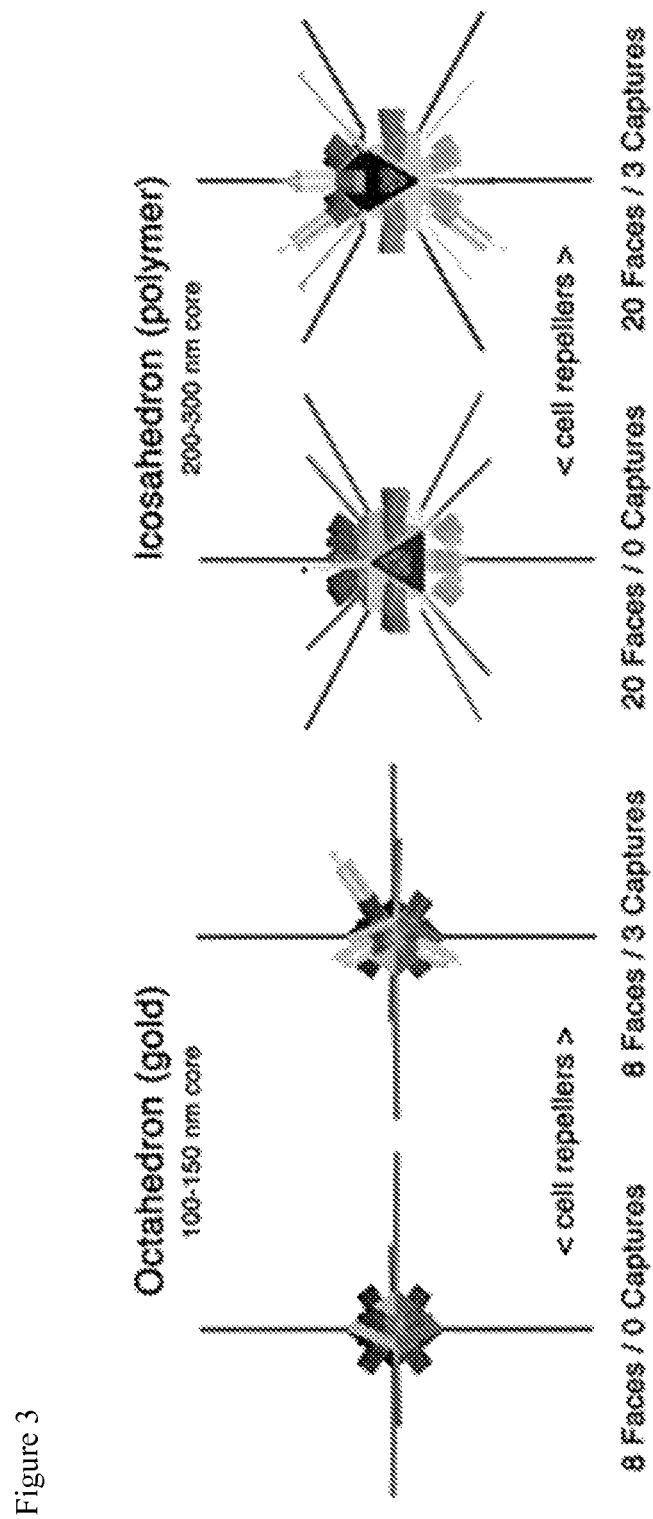

In some embodiments, the disclosure features a collection or plurality of particles having a defined mean particle size. As used herein, "mean particle size" is arrived at by measuring the size of individual particles and then dividing by the total number of particles. The determination of mean particle size is well known in the art. Typically, the longest average dimension of the particles is no greater than 1 μm. In some embodiments, the particles are nanoparticles. In some embodiments, the longest average dimension of the particles is no greater than 900 (e.g., 850, 800, 750, 700, 650, 600, 550, 500, 450, 400, 450, 400, 350, 300, 250, 200, or 150) nm. In some embodiments, a particle is shaped and sized to circulate in the blood or vasculature (e.g., arteries, veins, and capillaries) of a subject (e.g., a human subject). Exemplary particle designs are set forth in FIGS. 1 to 3.

In some embodiments, a plurality of the particles are polyhedral, e.g., cubic. In some embodiments, a plurality of the particles are spherical. In some embodiments, any of the particles described herein can be porous. Such porous particles comprise an outer surface and inner surfaces of the pores of the particle. The agent can be, e.g., immobilized on the inner surfaces. In some embodiments, a plurality of pores have a cross-sectional dimension of at least 50 nm. In some embodiments, a plurality of pores have a cross-sectional dimension of at least 100 nm. Porous nanoparticles have been described in, e.g., U.S. Patent Application Publication Nos. 20140199352, 20080277346, and 20040105821, the disclosures of each of which are incorporated by reference in their entirety. Spherical particles are described in, e.g., U.S. Pat. Nos. 8,778,830 and 8,586,096, each of which is hereby incorporated by reference.

In some embodiments, spherical particles can further comprise two intersecting ridges extending from the spherical surface of the particle, wherein the longest dimension of each of the structures is no greater than 1 μm, and wherein the ridges are sized and oriented: (i) to inhibit the agent immobilized on the surface of the spherical particle from binding to, or activating, a cell surface receptor protein and/or (ii) when the soluble biomolecule is bound to the agent, to inhibit the interaction of the soluble biomolecule and a second member of a specific binding pair of which the soluble biomolecule is the first member.

In some embodiments, a plurality of particles are toroidal. In such embodiments, the agent can be immobilized on an inner circumferential surface of the particle (e.g., around the hole—see FIG. 2). In some embodiments, the diameter of the particle is no greater than 600 (e.g., 550, 500, 450, 400, 350, 300, 200, or 150) nm.

In some embodiments, the particles described herein are dendritic. Such particles are described in, e.g., Du et al. (2015) *Small* 11(4):392-413; U.S. Pat. Nos. 5,814,272 and 7,932,311; and U.S. Patent Application Publication No. 20040166166, the disclosures of each of which are incorporated by reference herein. As elaborated on below, in some embodiments the geometry of the dendritic particles is such that the agent immobilized on the inner surface of the particle has a reduced, or substantially reduced, ability to interact with a biomolecule on the surface of a cell and/or the soluble biomolecule bound to the particle by virtue of the agent has a reduced, or substantially reduced, ability to interact with its cognate ligand (the second member of the specific binding pair).

In some embodiments, a plurality of particles are polyhedral, e.g., octahedral or icosahedral (see, e.g., FIG. 3), whether regular or irregular. The particles may comprise at least one protrusion from at least one of their vertices (see, e.g., FIG. 3). The particles may comprise more than one (e.g., 2, 3, 4, 5, 6, 7, or 8 or more) protrusion from their vertices. Such protrusions can be, e.g., sized and/or oriented: (i) to inhibit the agent immobilized on the surface of the spherical particle from binding to, or activating, a cell surface receptor protein and/or (ii) when the soluble biomolecule is bound to the agent, to inhibit the interaction of the soluble biomolecule and a second member of a specific binding pair of which the soluble biomolecule is the first member.

III. Particles Comprising Pores

In some embodiments, the material used to make the particles (e.g., silicon) may have a porosity of about 40% to about 95%, such as about 60% to about 80%. Porosity, as used herein, is a measure of the void spaces in a material, and is a fraction of the volume of voids over the total volume of the material. In certain embodiments, the carrier material has a porosity of at least about 10%, at least about 20%, at least about 30%, at least about 40%, at least about 50%, at least about 60%, at least about 70%, at least about 80%, or even at least about 90%. In particular embodiments, the porosity is greater than about 40%, such as greater than about 50%, greater than about 60%, or even greater than about 70%.

In certain embodiments, the agent is distributed to a pore depth from the surface of the material of at least about 0.005 microns, at least 0.05 microns, at least about 0.1 microns, at least about 0.2 microns, at least about 0.3 microns, at least about 0.4 microns, at least about 0.5 microns, at least about 0.6 microns, or at least about 0.7 microns. In certain embodiments, the agent is distributed in the pores of the carrier material substantially uniformly.

The agent may be loaded into the particle to a depth which is measured as a ratio to the total width of the particle. In certain embodiments, the agent is distributed to a depth of at least about 10% into the particle, to at least about 20% into the particle, at least about 30% into the particle, at least about 40% into the particle, at least about 50% into the particle, or at least about 60% into the particle.

The pore size may be preselected to the dimensional characteristics of the agent and target biomolecule to control the release of the biomolecule. Typically, pore sizes that are too small preclude loading of the agent and/or binding of the biomolecule. For example, the average pore diameter for a material may be selected from larger pores, e.g., 15 nm to 40 nm, for high molecular weight molecules, e.g., 200,000-500,000 amu, and smaller pores, e.g., 2 nm to 10 nm, for molecules of a lower molecular weight, e.g., 10,000-50,0000 amu. For instance, average pore sizes of about 6 nm in diameter may be suitable for molecules of molecular weight around 14,000 to 15,000 amu such as about 14,700 amu. Average pore sizes of about 10 nm in diameter may be selected for molecules of molecular weight around 45,000 to 50,000 amu such as about 48,000 amu. Average pore sizes of about 25-30 nm in diameter may be selected for molecules of molecular weight around 150,000 nm.

The pore size may be preselected to be adapted to the molecular radii of the agent or biomolecule. For instance, average pore sizes of about 25 nm to about 40 nm in diameter may be suitable for molecules with a largest molecular radius from about 6 nm to about 8 nm. Molecular radii may be calculated by any suitable method such as by using the physical dimensions of the molecule based on the X-ray crystallography data or using the hydrodynamic radius which represents the solution state size of the molecule. As the solution state calculation is dependent upon the nature of the solution in which the calculation is made, it may be preferable for some measurements to use the physical dimensions of the molecule based on the X-ray crystallography data. As used herein the largest molecular radius reflects half of the largest dimension of the therapeutic agent.

In certain embodiments, the average pore diameter is selected to limit the aggregation of molecules, e.g., proteins, within a pore. It would be advantageous to prevent biomolecules such as proteins from aggregating in a carrier material as this is believed to impede the controlled release of molecules into a biological system. Therefore, a pore that, due to the relationship between its size and the size of a biomolecule, allows, for example, only one biomolecule to enter the pore at any one time, will be preferable to a pore that allows multiple biomolecules to enter the pore together and aggregate within the pore. In certain embodiments, multiple biomolecules may be loaded into a pore, but due to the depth of the pore, the proteins distributed throughout this depth of the pore will aggregate to a lesser extent.

IV. Agent

In some embodiments, the geometry of the particle is such that the immobilized agent has a reduced, or substantially reduced, ability to interact with a biomolecule on the surface of a cell. For example, in some embodiments, TNFα or IL-2 immobilized on the surface of a particle described herein has less than 50 (e.g., 45, 40, 35, 30, 25, 20, 15, 10, 9, 8, 7, 6, 5, 4, 3, 2, or 1) % of the ability of free TNFα or IL-2 to bind to a TNFα receptor or IL-2 receptor on the surface of a cell. In some embodiments, the soluble biomolecule bound to the particle has a reduced, or substantially reduced, ability to interact with its cognate ligand (the second member of the specific binding pair). For example, a soluble TNFR bound to a particle described herein has less than 50 (e.g., 45, 40, 35, 30, 25, 20, 15, 10, 9, 8, 7, 6, 5, 4, 3, 2, or 1) % of the ability of free, soluble TNFR to interact with free TNFα. In another example, a soluble virion bound to a particle described herein has less than 50 (e.g., 45, 40, 35, 30, 25, 20, 15, 10, 9, 8, 7, 6, 5, 4, 3, 2, or 1) % of the ability of free virion to interact with its cognate cell surface receptor(s) and infect a cell. Exemplary particle geometries capable of reducing or substantially reducing the interaction of an agent with a biomolecule on a cell surface, or the interaction between a biomolecule bound to the particle, and its cognate ligand, are set forth in FIGS. 1 to 3 and described herein.

In some embodiments, the agent immobilized on the surface of a particle is a small molecule, a macrocycle compound, a polypeptide, a peptidomimetic compound, an aptamer, a nucleic acid, or a nucleic acid analog. "Small molecule" as used herein, is meant to refer to an agent, which has a molecular weight of less than about 6 kDa and most preferably less than about 2.5 kDa. Many pharmaceutical companies have extensive libraries of chemical and/or biological mixtures comprising arrays of small molecules, often fungal, bacterial, or algal extracts, which can be screened with any of the assays of the application. This application contemplates using, among other things, small chemical libraries, peptide libraries, or collections of natural products. Tan et al. described a library with over two million synthetic compounds that is compatible with miniaturized cell-based assays (*J Am Chem Soc* (1998) 120:8565-8566).

Peptidomimetics can be compounds in which at least a portion of a subject polypeptide is modified, and the three dimensional structure of the peptidomimetic remains substantially the same as that of the subject polypeptide. Peptidomimetics may be analogues of a subject polypeptide of the disclosure that are, themselves, polypeptides containing one or more substitutions or other modifications within the subject polypeptide sequence. Alternatively, at least a portion of the subject polypeptide sequence may be replaced with a non-peptide structure, such that the three-dimensional structure of the subject polypeptide is substantially retained. In other words, one, two or three amino acid residues within the subject polypeptide sequence may be replaced by a non-peptide structure. In addition, other peptide portions of the subject polypeptide may, but need not, be replaced with a non-peptide structure. Peptidomimetics (both peptide and non-peptidyl analogues) may have improved properties (e.g., decreased proteolysis, increased retention or increased bioavailability). Peptidomimetics generally have improved oral availability, which makes them especially suited to treatment of humans or animals. It should be noted that peptidomimetics may or may not have similar two-dimensional chemical structures, but share common three-dimensional structural features and geometry. Each peptidomimetic may further have one or more unique additional binding elements.

Aptamers are short oligonucleotide sequences that can be used to recognize and specifically bind almost any molecule, including cell surface proteins. The systematic evolution of ligands by exponential enrichment (SELEX) process is powerful and can be used to readily identify such aptamers, Aptamers can be made fir a wide range of proteins of importance for therapy and diagnostics, such as growth factors and cell surface antigens. These oligonucleotides bind their targets with similar affinities and specificities as antibodies do (see, e.g., Ulrich (2006) *Handb Exp Pharmacol* 173:305-326).

As noted above, the term "antibody" refers to whole antibodies including antibodies of different isotypes, such as IgM, IgG, IgA, IgD, and IgE antibodies. The term "antibody" includes a polyclonal antibody, a monoclonal antibody, a chimerized or chimeric antibody, a humanized antibody, a primatized antibody, a deimmunized antibody, and a fully human antibody. The antibody can be made in or derived from any of a variety of species, e.g., mammals such as humans, non-human primates (e.g., orangutan, baboons, or chimpanzees), horses, cattle, pigs, sheep, goats, dogs, cats, rabbits, guinea pigs, gerbils, hamsters, rats, and mice. The antibody can be a purified or a recombinant antibody.

The term "antibody fragment," "biomolecule-binding fragment," or similar terms refer to a fragment of an antibody that retains the ability to bind to a target antigen. Such fragments include, e.g., a single chain antibody, a single chain Fv fragment (scFv), an Fd fragment, an Fab fragment, an Fab' fragment, or an F(ab')$_2$ fragment. An scFv fragment is a single polypeptide chain that includes both the heavy and light chain variable regions of the antibody from which the scFv is derived. In addition, intrabodies, minibodies, triabodies, and diabodies are also included in the definition of antibody and are compatible for use in the methods described herein (see, e.g., Todorovska et al. (2001) *J Immunol Methods* 248(1):47-66; Hudson and Kortt (1999) *J Immunol Methods* 231(1):177-189; Poljak (1994) *Structure* 2(12):1121-1123; Rondon and Marasco (1997) *Annual Review of Microbiology* 51:257-283, the disclosures of each of which are incorporated herein by reference in their entirety). Bispecific antibodies (including DVD-Ig antibodies) are also embraced by the term "antibody." Bispecific antibodies are monoclonal, preferably human or humanized, antibodies that have binding specificities for at least two different antigens.

As used in herein, the term "antibody" also includes, e.g., single domain antibodies such as camelized single domain antibodies. See, e.g., Muyldermans et al. (2001) *Trends Biochem Sci* 26:230-235; Nuttall et al. (2000) *Curr Pharm Biotech* 1:253-263; Reichmann et al. (1999) *J Immunol Meth* 231:25-38; PCT application publication nos. WO 94/04678 and WO 94/25591; and U.S. Pat. Nos. 6,005,079, 6,015,695, and 7,794,981, all of which are incorporated herein by reference in their entireties. In some embodiments, the disclosure provides single domain antibodies comprising two VH domains with modifications such that single domain antibodies are formed.

In some embodiments, the agent is a non-antibody, scaffold protein. These proteins are, generally, obtained through combinatorial chemistry-based adaptation of pre-existing ligand- or antigen-binding proteins. For example, the binding site of human transferrin for human transferrin receptor can be modified using combinatorial chemistry to create a diverse library of transferrin variants, some of which have acquired affinity for different antigens (see Ali et al. (1999) *J Biol Chem* 274:24066-24073). The portion of human transferrin not involved with binding the receptor remains unchanged and serves as a scaffold, like framework regions of antibodies, to present the variant binding sites. The libraries are then screened, as an antibody library is, against a target antigen of interest to identify those variants having optimal selectivity and affinity for the target antigen. Non-antibody scaffold proteins, while similar in function to antibodies, are touted as having a number of advantages as compared to antibodies, which advantages include, among other things, enhanced solubility and tissue penetration, less costly manufacture, and ease of conjugation to other molecules of interest (see Hey et al. (2005) *TRENDS Biotechnol* 23(10):514-522).

One of skill in the art would appreciate that the scaffold portion of the non-antibody scaffold protein can include, e.g., all or part of: the Z domain of *S. aureus* protein A, human transferrin, human tenth fibronectin type III domain, kunitz domain of a human trypsin inhibitor, human CTLA-4, an ankyrin repeat protein, a human lipocalin, human crystallin, human ubiquitin, or a trypsin inhibitor from *E. elaterium* (see Hey et al. (2005) *TRENDS Biotechnol* 23(10): 514-522).

In some embodiments, the agent is a natural ligand of a target biomolecule. For example, the agent can be a cytokine. As used herein, the term "cytokine" refers to any secreted polypeptide that affects the functions of cells and is a molecule which modulates interactions between cells in the immune, inflammatory or hematopoietic response. A cytokine includes, but is not limited to, monokines and lymphokines, regardless of which cells produce them. For instance, a monokine is generally referred to as being produced and secreted by a mononuclear cell, such as a macrophage and/or monocyte. Many other cells however also produce monokines, such as natural killer cells, fibroblasts, basophils, neutrophils, endothelial cells, brain astrocytes, bone marrow stromal cells, epidermal keratinocytes and B-lymphocytes. Lymphokines are generally referred to as being produced by lymphocyte cells. Examples of cytokines include, but are not limited to, Interleukin-1 (IL-1), Interleukin-2 (IL-2), Interleukin-6 (IL-6), Interleukin-8 (IL-8), Tumor Necrosis Factor-alpha (TNF-α), and Tumor Necrosis Factor beta (TNF-β).

In some embodiments, the agent is a tumor necrosis factor (TNF) family ligand, e.g., the TNF family ligand is selected from TNFα, TNFβ, Fas ligand, lymphotoxin, lymphotoxin alpha, lymphotoxin beta, 4-1BB Ligand, CD30 Ligand, EDA-A1, LIGHT, TLA1, TWEAK, TNFβ, and TRAIL.

In some embodiments, the agent is a variant of a natural ligand for a target biomolecule, e.g., a variant interleukin polypeptide, such as variant IL-2 or variant TNFα. Variants, in accordance with some embodiments of the invention, can contain one or more amino acid substitutions, deletions, or insertions. The substitutions can be conservative or non-conservative. As used herein, the term "conservative substitution" refers to the replacement of an amino acid present in the native sequence in a given polypeptide with a naturally or non-naturally occurring amino acid having similar steric properties. Where the side-chain of the native amino acid to be replaced is either polar or hydrophobic, the conservative substitution should be with a naturally occurring amino acid or a non-naturally occurring amino acid that is also polar or hydrophobic, and, optionally, with the same or similar steric properties as the side-chain of the replaced amino acid. Conservative substitutions typically include substitutions within the following groups: glycine and alanine; valine, isoleucine, and leucine; aspartic acid and glutamic acid; asparagine, glutamine, serine, and threonine; lysine, histidine, and arginine; and phenylalanine and tyrosine. One letter amino acid abbreviations are as follows: alanine (A); arginine (R); asparagine (N); aspartic acid (D); cysteine (C); glycine (G); glutamine (Q); glutamic acid (E); histidine (H); isoleucine (I); leucine (L); lysine (K); methionine (M); phenylalanine (F); proline (P); serine (S); threonine (T); tryptophan (W), tyrosine (Y); and valine (V). Variants also include fragments of the full-length, wild-type natural ligands as well as fragments comprising one or more amino acid substitutions, insertions, or deletions relative to the wild-type, full-length natural ligand from which the fragment was derived.

The phrase "non-conservative substitutions" as used herein refers to replacement of the amino acid as present in the parent sequence by another naturally or non-naturally occurring amino acid, having different electrochemical and/or steric properties. Thus, the side chain of the substituting amino acid can be significantly larger (or smaller) than the side chain of the native amino acid being substituted and/or can have functional groups with significantly different electronic properties than the amino acid being substituted.

In some embodiments, a variant polypeptide comprises at least two (e.g., at least three, four, five, six, seven, eight, nine, 10, 15, 20, 25, 30, 35, 40, 45, 50, 55, 60, 65, 70, 75, 80, 85, 90, 95, 100, or more than 100) amino acid substitutions, deletions, or insertions, relative to the wild-type, full-length polypeptide from which it was derived. In some embodiments, a variant polypeptide comprises no more than 150 (e.g., no more than 145, 140, 135, 130, 125, 120, 115, 110, 105, 100, 95, 90, 85, 80, 75, 70, 65, 60, 55, 50, 45, 40, 35, 30, 25, 24, 23, 22, 21, 20, 19, 18, 17, 16, 15, 14, 13, 12, 11, 10, 9, 8, 7, 6, 5, 4, 3, or 2) amino acid substitutions, deletions, or insertions, relative to the wild-type, full-length polypeptide from which it was derived.

In some embodiments, a variant polypeptide (e.g., a variant IL-2 or TNFα polypeptide) retains at least 10 (e.g., at least 15, 20, 25, 30, 35, 40, 45, 50, 55, 60, 65, 70, 75, 80, 85, 90, 95, or 100) % of the ability of the wild-type, full-length polypeptide from which it was derived to bind to the target biomolecule (e.g., the member of the specific binding pair of which the wild-type, full-length polypeptide is a member). In some embodiments, the variant polypeptide will have a greater affinity for the target biomolecule than the wild-type, full-length polypeptide from which the variant was derived. For example, in some embodiments, the variant polypeptide has two (three, four, five, 10, 20, 30, 40, 50, 100, 200, 500, or even 1000) times greater affinity for the target biomolecule than does the wild-type, full-length polypeptide from which the variant polypeptide was derived. Methods for detecting or measuring the interaction between two proteins are known in the art and described above.

In some embodiments, the wild-type, full-length natural ligand modulates the activity of a cell surface receptor. Accordingly, variants of the natural ligands can have enhanced or reduced ability to modulate the activity of the receptor, relative to the activity of the wild-type natural ligand. For example, in some embodiments, a variant polypeptide has less than 90 (e.g., 85, 80, 75, 70, 65, 60, 55, 50, 45, 40, 35, 30, 25, 20, 15, 10, or less than 5) % of the ability of the full-length, wild-type polypeptide from which the variant was derived to activate a cell surface receptor protein. In some embodiments, the variant polypeptide does not activate the receptor to which it binds.

Such exemplary variant polypeptides are known in the art. For example, International Patent Application Publication No. WO 2012/085891 describes TNF family ligand variants having reduced ability to trimerize, and thus a reduced ability to activate TNF family receptors (see also U.S. Patent Application Publication No. U.S. 2014/0096274, hereby incorporated by reference). Yet the variant TNF ligands retain the ability to bind to TNF family receptors. Suitable methods for comparing activity between variant and wild-type natural ligands are known in the art.

In some embodiments, the soluble biomolecule is a ligand for a cell surface receptor, e.g., a cytokine or chemokine, such as any of those known in the art or described herein. In some embodiments, the ligand is a tumor necrosis factor (TNF) family ligand or a variant thereof. In some embodiments, the TNF family ligand is TNFα or a variant thereof. In some embodiments, the TNF family ligand is Fas ligand, lymphotoxin, lymphotoxin alpha, lymphotoxin beta, 4-1BB Ligand, CD30 Ligand, EDA-A1, LIGHT, TLA1, TWEAK, TNFβ, TRAIL, or a variant of any of the foregoing.).

In some embodiments, the soluble biomolecule is one identified in Table 2.

TABLE 2

Exemplary Soluble Biomolecules and/or Agents

| First Member of Specific Binding Pair (Soluble Biomolecule or Agent) | Gene Abbrev. | Molecule Class | Associated Disease State | Second member of Specific Binding Pair |
|---|---|---|---|---|
| Tumor Necrosis Factor alpha | TNF | Cytokine | AD | sTNF-R |
| Soluble Interleukin-2 receptor | IL2RA | Decoy | Cancer | sIL-2R |
| Soluble Tumor Necrosis Factor receptor-1 | TNFRSF1A | Decoy | Cancer | rTNF |
| Soluble Tumor Necrosis Factor receptor-2 | TNFRSF1B | Decoy | Cancer | rTNF |
| Interleukin-2 | IL2 | Cytokine | AD | sIL-2R |
| Interleukin-6 | IL6 | Cytokine | AD | sIL-6R |
| Interleukin-8 | CXCL8 | Cytokine | AD | sIL-8R |
| Interleukin-1A | IL1A | Cytokine | AD | sIL-1RA |
| Interleukin-1B | IL1B | Cytokine | Inflammation | |
| C—X—C motif chemokine 10 | CXCL10 | Chemokine | Immune activation | CXCR3 |
| Decoy receptor-3 | FAS | Decoy | Cancer | FAS-L |
| Soluble death receptor-4 | TNFRSF10A | Decoy | Cancer | TRAIL-R1 |
| Soluble death receptor-5 | TNFRSF10B | Decoy | Cancer | TRAIL-R2 |
| Fas ligand | FASLG | Cytokine | AD | sDcR3 |
| TNF-related apoptosis inducing ligand | TNFSF10 | Cytokine | AD | sDR4/5 |
| Chemokine (C—X—C Motif) Ligand 1 (Melanoma Growth Stimulating Activity, Alpha) | CXCL1 | Chemokine | Cancer | |
| TNF-related weak inducer of apoptosis | TNFSF12 | Cytokine | TBD | sDR3 |
| Matrix Metallopeptidase 1 (Interstitial Collagenase) | MMP1 | Protease | Cancer | |
| Matrix Metallopeptidase 2 (Gelatinase A, 72 kDa Gelatinase, 72 kDa Type IV Collagenase) | MMP2 | Protease | OA/Cancer | |
| Matrix Metallopeptidase 3 (Stromelysin 1, Progelatinase) | MMP3 | Protease | Cancer | |
| Matrix Metallopeptidase 9 | MMP9 | Protease | OA/Cancer | |

TABLE 2-continued

Exemplary Soluble Biomolecules and/or Agents

| First Member of Specific Binding Pair (Soluble Biomolecule or Agent) | Gene Abbrev. | Molecule Class | Associated Disease State | Second member of Specific Binding Pair |
|---|---|---|---|---|
| (Gelatinase B, 92 kDa Gelatinase, 92 kDa Type IV Collagenase) | | | | |
| Matrix Metallopeptidase 10 (Stromelysin 2) | MMP10 | Protease | Cancer | |
| Matrix Metallopeptidase 12 (Macrophage Elastase) | MMP12 | Protease | Cancer | |
| Indoleamine 2,3-dioxygenase | IDO1 | Enzyme | Cancer | |
| Interleukin-5 | IL5 | Cytokine | AD | Mepolizumab |
| Soluble Interleukin-5 receptor | IL5RA | Decoy | Cancer | IL-5 |
| Soluble interleukin-6 receptor | IL6R | Decoy | Cancer | IL-6 |
| Soluble interleukin-8 receptor | CXCR1 | Decoy | Cancer | IL-8 |
| Soluble interleukin-1A receptor | IL1R1 | Decoy | Cancer | IL-1A |
| C-Reactive Protein | CRP | Protein | Marker of inflammation | |
| Soluble death receptor-3 | TNFRSF25 | Decoy | | TWEAK |

"AD" refers to autoimmune disorders and/or inflammatory disorders.
"OA" refers to osteoarthritis.

In some embodiments, each particle comprises a plurality of agents. The plurality of agents may comprise 10 to about $10^9$ copies of the agent, such as about $10^3$ to about $10^7$ copies of the agent or about $10^4$ to about $10^6$ copies of the agent.

V. Methods for Producing an Antibody

As noted above, in some embodiments the agents immobilized on the surface of the particle or particles is an antibody or antigen-binding fragment thereof. Antibodies may be elicited by methods known in the art. For example, a mammal, such as a mouse, a hamster or rabbit, may be immunized with an immunogenic form of a soluble biomolecule (e.g., a soluble TNFR, a toxin, or a viral protein). Alternatively, immunization may occur by using a nucleic acid, which in vivo expresses a biomolecule (e.g., a soluble protein) giving rise to the immunogenic response observed. Techniques for conferring immunogenicity on a protein or peptide include conjugation to carriers or other techniques well known in the art. For instance, a peptidyl portion of a polypeptide of the invention may be administered in the presence of adjuvant. The progress of immunization may be monitored by the detection of antibody titers in plasma or serum. Standard ELISA or other immunoassays may be used with the immunogen as antigen to assess the levels of antibodies.

Following immunization, antisera reactive with a polypeptide of the invention may be obtained and, if desired, polyclonal antibodies isolated from the serum. To produce monoclonal antibodies, antibody producing cells (lymphocytes) may be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) Nature, 256: 495-497), as the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77-96). Hybridoma cells can be screened immunochemically for production of antibodies specifically reactive with the polypeptides of the invention and the monoclonal antibodies isolated.

VI. Particle Clearance

In some embodiments, a particle comprises a clearance agent. The clearance agent may facilitate clearance of the particle through a biological pathway, such as by excretion in the urine, degradation, excretion by a hepatobiliary pathway, and/or phagocytosis.

For example, the particle may comprise a reservoir, wherein the reservoir comprises a clearance agent. The reservoir may be a hole or void in the body of a particle, e.g., a void in the body of a porous silicon particle.

For particles comprising pores, the reservoir may be a pore or the reservoir may be larger or smaller than the average pore size. A reservoir may consist of a recess in the body of a particle (e.g., a shallow recess), wherein the width or diameter of the recess is larger than the width or diameter of the average pore size. The width or diameter of a reservoir may be at least about 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 90, 100, 110, 120, 130, 140, 150, 175, 200, 250, 300, 400, or even about 500 times as large as the width or diameter of the average pore size. The width or diameter of the reservoir may be about 2 times to about 10 times the width or diameter of the average pore size, such as about 2 times to about 8 times or about 2 times to about 6 times. The width or diameter of a reservoir may be about 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 90, 100, 110, 120, 130, 140, 150, 175, 200, 250, 300, 400, or even about 500 times as large as the width or diameter of the average pore size.

The reservoir may comprise an opening. The opening may be covered by a cap or member, thereby inhibiting interactions between the clearance agent and cells and/or extracellular proteins (e.g., antibodies). The cap or member may comprise a polymer, such as a biodegradable polymer. The cap or member may degrade after a predetermined period of time (e.g., by hydrolysis), thereby exposing the clearance agent to cells and/or extracellular proteins. The cap or member may degrade after exposure to a biological fluid (e.g., blood plasma or extracellular fluid) for about 1 day to about 5 years, such as about 1 day to about 3 years, or about 1 day to about 1 year.

A predetermined period of time may be a period of time that the particle is in a liquid (e.g., an aqueous liquid). The predetermined period of time may be a period of in vivo residence of a particle (e.g., exposure to biological fluids, pH, enzymes, and/or temperatures). The predetermined period of time may be determined, at least in part, by the binding of the particle to a biomolecule. For example, the particle may be configured such that the binding of a biomolecule exposes the clearance agent to cells and/or extracellular proteins (see, e.g., PCT Patent Application Publication No. WO2014/170899, hereby incorporated by reference). The predetermined period of time may be about 1 day to about 5 years, such as about 1 day to about 3 years, or about 1 day to about 1 year.

Exemplary materials suitable for use as caps or membranes, are described in U.S. Pat. No. 7,918,842, which is hereby incorporated by reference. In general, these materials degrade or dissolve either by enzymatic hydrolysis or exposure to water in vivo or in vitro, or by surface or bulk erosion. Representative synthetic, biodegradable polymers include: poly(amides) such as poly(amino acids) and poly(peptides); poly(esters) such as poly(lactic acid), poly(glycolic acid), poly(lactic-co-glycolic acid), and poly(caprolactone); poly(anhydrides); poly(orthoesters); poly(carbonates); and chemical derivatives thereof (substitutions, additions of chemical groups, for example, alkyl, alkylene, hydroxylations, oxidations, and other modifications routinely made by those skilled in the art), copolymers and mixtures thereof. Other polymers that may be used in caps or membranes include: poly(ethers) such as poly(ethylene oxide), poly(ethylene glycol), and poly(tetramethylene oxide); vinyl polymers—poly(acrylates) and poly(methacrylates) such as methyl, ethyl, other alkyl, hydroxyethyl methacrylate, acrylic and methacrylic acids, and others such as poly(vinyl alcohol), poly(vinyl pyrolidone), and poly(vinyl acetate); poly(urethanes); cellulose and its derivatives such as alkyl, hydroxyalkyl, ethers, esters, nitrocellulose, and various cellulose acetates; poly(siloxanes); and any chemical derivatives thereof (substitutions, additions of chemical groups, for example, alkyl, alkylene, hydroxylations, oxidations, and other modifications routinely made by those skilled in the art), copolymers and mixtures thereof. In certain embodiments, the reservoir cap is formed from one or more cross-linked polymers, such as cross-linked polyvinyl alcohol.

In some embodiments, a particle comprises a coating. In some embodiments, the coating comprises a clearance agent. The coating may mask a clearance agent.

The particle may comprise a first surface and a second surface; the agent may be immobilized on the first surface; and the coating may cover at least a portion of the second surface. The first surface may be an interior surface or an inner surface, e.g., the first surface may be oriented such that the agent has a reduced ability to bind to a molecule on a cell surface. Examples of an interior surface or inner surface include the inner walls of a pore, reservoir, or tube, the inner circumferential surface of a toroid, or the hollow of a concave surface. Other examples of an interior surface or inner surface include the outer surface of a particle, wherein the outer surface is protected from interactions with cells by one or more protrusions. The second surface may be an exterior surface, e.g., the second surface may be oriented such that the coating can interact with a cell.

A coating may inhibit interactions between particles, e.g., the coating may reduce the propensity of particles to form aggregates. The coating may inhibit interactions between a particle and cells, e.g., by presenting a biologically-inert surface. The coating may inhibit non-specific interactions with extracellular molecules, e.g., non-specific adsorption of biomolecules. A coating may inhibit specific interactions with cells or extracellular molecules, e.g., a coating may disfavor or delay the excretion or phagocytosis of a particle. A coating may target a particle for excretion or phagocytosis. A coating or other feature (e.g., an "excretion-inducing compound") that targets a particle for excretion or phagocytosis may be masked by a coating (e.g., a second coating) that delays the excretion or phagocytosis of the particle, e.g., to promote maintenance of the particles in the bloodstream for a predetermined amount of time.

A particle may comprise a second coating, e.g., wherein the second coating consists of a second plurality of coating molecules. A particle may comprise a second plurality of coating molecules. The second coating and/or second plurality of coating molecules may decrease the clearance of the particle in vivo, e.g., by masking the coating and/or plurality of coating molecules. The second coating and/or second plurality of coating molecules may be biodegradable, e.g., to expose the coating and/or plurality of coating molecules to cells and/or extracellular proteins after a predetermined period of time. The second coating and/or second plurality of coating molecules may comprise a biodegradable polymer, e.g., each molecule of the second plurality of coating molecules may comprise a biodegradable polymer. The second coating and/or second plurality of coating molecules may comprise CD47, which inhibits phagocytosis.

In some embodiments, the particle comprises a first surface (e.g., an interior surface) and a second surface (e.g., an exterior surface); the agent is immobilized on the first surface; and the coating covers at least a portion of the second surface. The orientation of the first surface may reduce the ability of the agent to interact with molecules on a cell surface. The orientation of the second surface may permit interactions between the coating and cells, extracellular molecules, and/or different particles. An "interaction" between the coating and cells, extracellular molecules, and/or different particles may be a weak, neutral, or unfavorable interaction, e.g., to disfavor stable binding of the particle to a cell, extracellular molecule, or other particle. Alternatively, an interaction between the coating and either cells and/or extracellular molecules may be a specific or designed interaction, e.g., to favor clearance of the particle through a biological pathway, such as phagocytosis. In certain preferred embodiments, the second surface is substantially free of agent. In certain preferred embodiments, the first surface is substantially free of coating. In certain preferred embodiments, the coating covers substantially all of the second surface.

In some embodiments, the particle comprises a first surface (e.g., an interior surface) and a second surface (e.g., an exterior surface); the agent is immobilized on the first surface and the second surface; and the coating covers at least a portion of the second surface. In such embodiments, the coating (and/or a second coating) may inhibit interactions between the agent and molecules on a cell surface. In certain preferred embodiments, the coating covers substantially all of the second surface.

In some embodiments, the particle comprises a first surface (e.g., an interior surface) and a second surface (e.g., an exterior surface); the agent is immobilized on the first surface; and the coating covers at least a portion of the first surface and at least a portion of the second surface. In such embodiments, the coating preferably does not affect the ability of the agent to specifically bind to a biomolecule. In certain preferred embodiments, the coating covers substantially all of the second surface.

In some embodiments, the particle comprises a surface; the agent is immobilized on the surface; and the coating covers at least a portion of the surface. In such embodiments, the coating may not affect the ability of the agent to specifically bind to a biomolecule. The coating may allow for some of the agent to specifically bind to a biomolecule and inhibit interactions between some of the agent and biomolecule. The coating may inhibit interactions between the agent and molecules on a cell surface. In certain preferred embodiments, the coating covers substantially all of the surface.

A coating may comprise coating molecules, e.g., a coating may consist of a plurality of coating molecules or a coating may consist of a population of coating molecules. As used herein, the terms "plurality of coating molecules" and "population of coating molecules" each refer to a coating. The term "coating", however, may refer to additional compositions, such as a hydrogel. A coating molecule may be a clearance agent (and thus, a clearance agent may be a coating molecule).

A particle may comprise a plurality of coating molecules. The particle may comprise a surface and a plurality of agents immobilized on the surface, and at least one molecule of the plurality of coating molecules may be bound to the surface. For example, all or substantially all of the molecules of the plurality of coating molecules may be bound to the surface.

The particle may comprise a surface and a second surface, wherein a plurality of agents immobilized on the surface, and at least one molecule of the plurality of coating molecules may be bound to the second surface. For example, all or substantially all of the molecules of the plurality of coating molecules may be bound to the second surface. In some embodiments, some of the molecules of the plurality of coating molecules are bound to the surface and some of the molecules of the plurality of coating molecules are bound to the second surface.

In some embodiments, the coating molecules increase the clearance of the particle in vivo. For example, the coating molecules may comprise a pathogen-associated molecular pattern.

In some embodiments, the particles described herein have a coating comprising an excretion-inducing compound, which facilitates the removal of the particles from the circulation, e.g., via the kidneys, liver/intestines (e.g., via bile), or phagocytosis (e.g., by antigen-presenting cells). A plurality of coating molecules may be a plurality of excretion-inducing compounds. For example, in embodiments in which the particles are toroidal, the inner circumferential surface (e.g., a first surface) may comprise an immobilized agent and the outer surface (e.g., a second surface) may comprise a compound that induces the clearance of the particles, e.g., by the kidneys, liver, or macrophages. In some embodiments, the excretion-inducing compound is programmed. That is, the compound can be covered with a coating that degrades (e.g., through the action of enzymes, hydrolysis, or gradual dissolution) over time (e.g., a predetermined amount of time) eventually exposing the excretion-inducing compound or other feature that increases the rate of clearance. The coating may degrade after exposure to a biological fluid (e.g., blood plasma or extracellular fluid) for about 1 day to about 5 years, such as about 1 day to about 3 years, or about 1 day to about 1 year. Thus, the in vivo residence of a particle may be modified and/or controlled.

A coating may comprise an organic polymer, such as polyethylene glycol (PEG). An organic polymer may be attached to a particle, e.g., attached to a surface of the particle. The organic polymer may include PEG, polylactate, polylactic acids, sugars, lipids, polyglutamic acid, polyglycolic acid (PGA), polylactic acid (PLA), poly(lactic-co-glycolic acid) (PLGA), polyvinyl acetate (PVA), and combinations thereof. In certain embodiments, the particle is covalently conjugated with PEG, which discourages adsorption of serum proteins, facilitates efficient urinary excretion and decreases aggregation of the particle (see, e.g., Burns et al. *Nano Letters*, 9(1):442-448 (2009) and U.S. Patent Application Publication Nos. 2013/0039848 and 2014/0248210, each of which is hereby incorporated by reference).

In one embodiment, the coating comprises at least one hydrophilic moiety, for example, Pluronic® type polymers (a nonionic polyoxyethylene-polyoxypropylene block co-polymer with the general formula $HO(C_2H_4O)_a(-C_3H_6O)_b(C_2H_4O)_aH)$, a triblock copolymer poly(ethylene glycol-b-(DL-lactic acid-co-glycolic acid)-b-ethylene glycol) (PEG-PLGA-PEG), a diblock copolymer polycaprolactone-PEG (PCL-PEG), poly(vinylidene fluoride)-PEG (PVDF-PEG), poly(lactic acid-co-PEG) (PLA-PEG), poly(methyl methacrylate)-PEG (PMMA-PEG) and so forth. In an embodiment with such a moiety, the hydrophilic moiety is a PEG moiety such as: a [Methoxy(Polyethyleneoxy)Propyl]-Trimethoxysilane (e.g., $CH_3(OC_2H_4)_{6-9}(CH_2)OSi(OCH_3)_3$), a [Methoxy(Polyethyleneoxy)Propyl]-Dimethoxysilane (e.g., $CH_3(OC_2H_4)_{6-9}(CH_2)OSi(OCH_3)_2$), or a [Methoxy(Polyethyleneoxy)Propyl]-Monomethoxysilane (e.g., $CH_3(OC_2H_4)_{6-9}(CH_2)OSi(OCH_3)$). Suitable coatings are described, for example, in U.S. Patent Application Publication No. 2011/0028662 (hereby incorporated by reference).

The coating may include a polyhydroxylated polymer, such as natural polymers or hydroxyl-containing polymers including multiply-hydroxylated polymers, polysaccharides, carbohydrates, polyols, polyvinyl alcohol, poly amino acids such as polyserine, or other polymers such as 2-(hydroxyethyl)methacrylate, or combinations thereof. In some embodiments, the polyhydroxylated polymers are polysaccharides. Polysaccharides include, mannan, pullulan, maltodextrin, starches, cellulose, and cellulose derivatives, gums, xanthan gum, locust bean gum, or pectin, combinations thereof (see, e.g., U.S. Patent Application Publication No. 2013/0337070, hereby incorporated by reference).

In some embodiments, the coating comprises a zwitterionic polymer (see, e.g., U.S. Patent Application Publication Nos. 2014/0235803, 2014/0147387, 2013/0196450, and 2012/0141797; and U.S. Pat. No. 8,574,549, each of which is hereby incorporated by reference).

Other suitable coatings include poly-alpha hydroxy acids (including polyactic acid or polylactide, polyglycolic acid, or polyglycolide), poly-beta hydroxy acids (such as polyhydroxybutyrate or polyhydroxyvalerate), epoxy polymers (including polyethylene oxide (PEO)), polyvinyl alcohols, polyesters, polyorthoesters, polyamidoesters, polyester-amides, polyphosphoesters, and polyphosphoester-urethanes. Examples of degradable polyesters include: poly(hydroxyalkanoates), including poly(lactic acid) or (polylactide, PLA), poly(glycolic acid) or polyglycolide (PGA), poly(3-hydroxybutyrate), poly(4-hydroxybutyrate), poly(3-hydroxyvalerate), and poly(caprolactone), or poly(valerolactone). Examples of polyoxaesters include poly(alkylene oxalates) such as poly(ethylene oxalate)) and polyoxaesters containing amido groups. Other suitable coating materials include polyethers including polyglycols, ether-ester copolymers (copoly(ether-esters)) and polycarbonates. Examples of biodegradable polycarbonates include polyorthocarbonates, polyiminocarbonates, polyalkylcarbonates such as poly(trimethylene carbonate), poly(1,3- dioxan-2-one), poly(p-dioxanone), poly(6,6-dimethyl-1,4-dioxan-2-one), poly(1,4-dioxepan-2-one), and poly(1,5-dioxepan-2-one). Suitable biodegradable coatings can also include polyanhydrides, polyimines (such as poly(ethylene imine) (PEI)), polyamides (including poly-N-(2-hydroxypropyl)-methacrylamide), poly(amino acids) (including a polylysine such as poly-L-lysine, or a polyglutamic acid such as poly-L-glutamic acid), polyphosphazenes (such as poly(phenoxy-co-carboxylatophenoxy phosphazene), poly-organophosphazenes, polycyanoacrylates and polyalkylcyanoacrylates (including polybutylcyanoacrylate), polyisocyanates, and polyvinylpyrrolidones.

The chain length of a polymeric coating molecule may be about 1 to about 100 monomer units, such as about 4 to about 25 units.

A particle may be coated with a naturally occurring polymer, including fibrin, fibrinogen, elastin, casein, collagens, chitosan, extracellular matrix (ECM), carrageenan, chondroitin, pectin, alginate, alginic acid, albumin, dextrin, dextrans, gelatins, mannitol, n-halamine, polysaccharides, poly-1,4-glucans, starch, hydroxyethyl starch (HES), dialdehyde starch, glycogen, amylase, hydroxyethyl amylase, amylopectin, glucoso-glycans, fatty acids (and esters thereof), hyaluronic acid, protamine, polyaspartic acid, polyglutamic acid, D-mannuronic acid, L-guluronic acid, zein and other prolamines, alginic acid, guar gum, and phosphorylcholine, as well as co-polymers and derivatives thereof. The coating may also comprise a modified polysaccharide, such as cellulose, chitin, dextran, starch, hydroxyethyl starch, polygluconate, hyaluronic acid, and elatin, as well as co-polymers and derivative thereof.

A particle may be coated with a hydrogel. The hydrogel can be formed, for example, using a base polymer selected from any suitable polymer, such as poly(hydroxyalkyl (meth)acrylates), polyesters, poly(meth)acrylamides, poly (vinyl pyrrolidone), or polyvinyl alcohol. A cross-linking agent can be one or more of peroxides, sulfur, sulfur dichloride, metal oxides, selenium, tellurium, diamines, diisocyanates, alkyl phenyl disulfides, tetraalkyl thiuram disulfides, 4,4'-dithiomorpholine, p-quinine dioxime and tetrachloro-p-benzoquinone. Also, boronic acid-containing polymers can be incorporated in hydrogels, with optional photopolymerizable groups.

In certain preferred embodiments, the coating comprises a material that is approved for use by the U.S. Food and Drug Administration (FDA). These FDA-approved materials include polyglycolic acid (PGA), polylactic acid (PLA), Polyglactin 910 (comprising a 9:1 ratio of glycolide per lactide unit, and known also as VICRYL™), polyglyconate (comprising a 9:1 ratio of glycolide per trimethylene carbonate unit, and known also as MAXON™), and polydioxanone (PDS).

The attachment of a coating to a particle may be accomplished by a covalent bond or a non-covalent bond, such as by ionic bond, hydrogen bond, hydrophobic bond, coordination, adhesive, or physical absorption or interaction.

Conventional nanoparticle coating methods include dry and wet approaches. Dry methods include: (a) physical vapor deposition (Zhang, Y. et al. Solid State Commun. 115:51 (2000)), (b) plasma treatment (Shi, D. et al. Appl. Phys. Lett. 78:1243 (2001); Vollath, D. et al. J. Nanoparticle Res. 1:235 (1999)), (c) chemical vapor deposition (Takeo, O. et al. J. Mater. Chem. 8:1323 (1998)), and (d) pyrolysis of polymeric or non-polymeric organic materials for in situ precipitation of nanoparticles within a matrix (Sglavo, V. M. et al. J. Mater Sci. 28:6437 (1993)). Wet methods for coating particles include: (a) sol-gel processes and (b) emulsification and solvent evaporation techniques (Cohen, H. et al. Gene Ther. 7:1896 (2000); Hrkach, J. S. et al. Biomaterials 18:27 (1997); Wang, D. et al. J. Control. Rel. 57:9 (1999)). A coating may be applied by electroplating, spray coating, dip coating, sputtering, chemical vapor deposition, or physical vapor deposition. Additionally, methods for coating various nanoparticles with polysaccharides are known in the art (see, e.g., U.S. Pat. No. 8,685,538 and U.S. Patent Application Publication No. 2013/0323182, each of which is hereby incorporated by reference).

In some embodiments, the particles may be adapted to facilitate clearance by renal excretion. Renal clearance for subjects with normal renal function generally requires particles with at least one dimension that is less than 15 nm (see, e.g., Choi, H. S., et al. Nat Biotechnol 25(1):1165 (2007); Longmire, M. et al., Nanomedicine 3(5):703 (2008)). Nevertheless, larger particles may be excreted in the urine. For embodiments in which a particle is too large for renal clearance, the particle may nevertheless be cleared following in vivo degradation to a smaller size.

In some embodiments, the particles may be adapted to facilitate clearance by hepatobiliary excretion. The mononuclear phagocytic system (MPS), which includes the Kupffer cells in the liver, is involved in the liver uptake and subsequent biliary excretion of nanoparticles. Certain size and surface properties of nanoparticles are known to increase uptake by the MPS in the liver (see Choi et al., J. of Dispersion Sci. Tech. 24(3/4):475-487 (2003); and Brannon-Peppas et al., J. Drug Delivery Sci. Tech. 14(4):257-264 (2004), each of which is incorporated by reference). For example, increasing the hydrophobicity of a particle is known to increase uptake by the MPS. Thus, one of ordinary skill in the art can select for particles having certain characteristics to modulate biliary excretion. The hepatobiliary system allows for the excretion of particles that are somewhat larger than those that may be excreted through the renal system (e.g., 10 to 20 nm). For embodiments in which a particle is too large for hepatobiliary excretion, the particle may nevertheless be cleared following in vivo degradation to a smaller size. In such embodiments, a coating that facilitates clearance by hepatobiliary excretion may cover a portion of an inner surface of a particle such that the coating becomes exposed following degradation of the particle. The particle may comprise a plurality of coating molecules, e.g., hydrophobic molecules, that cover a portion of a surface. The surface may be exposed following degradation of the particle, allowing for clearance of the degraded particle.

In some embodiments, the particle is adapted to facilitate clearance by phagocytosis. For example, the particle may comprise a clearance agent, wherein the clearance agent comprises a pathogen-associated molecular pattern, e.g., for recognition by macrophages. Pathogen-associated molecular patterns (PAMPs) include unmethylated CpG DNA (bacterial), double-stranded RNA (viral), lipopolysacharride (bacterial), peptidoglycan (bacterial), lipoarabinomannan (bacterial), zymosan (yeast), mycoplasmal lipoproteins such as MALP-2 (bacterial), flagellin (bacterial), poly(inosinic-cytidylic) acid (bacterial), lipoteichoic acid (bacterial), and imidazoquinolines (synthetic). In preferred embodiments, the PAMP clearance agent is masked such that macrophages do not engulf the particle prior to the binding of the particle to one or more targets. For example, a PAMP clearance agent may be masked by any one of the aforementioned coatings (e.g., a polymeric coating, such as a biodegradable polymeric coating). Macrophages can engulf particles as large as 20 μm (see, e.g., Cannon, G. J. and Swanson, J. A., J. Cell Science 101:907-913 (1992); Champion, J. A., et al.

Pharm Res 25(8):1815-1821 (2008)). In some embodiments, a clearance agent that facilitates clearance by phagocytosis may cover a portion of an inner surface of a particle such that the clearance agent becomes exposed following degradation of the particle. The particle may comprise a plurality of clearance agents, e.g., PAMPs, that cover a portion of a surface. The surface may be exposed following degradation of the particle, allowing for clearance of the degraded particle. The clearance agent may cover a portion of a surface that overlaps a surface comprising an agent. The clearance agent (e.g., PAMPs) may elicit an immune response against the particle, e.g., following the degradation of a second coating or following the degradation of the particle.

In some embodiments, an immune response directed against a clearance agent (e.g. PAMPs) may outcompete an immune response directed against the agent and/or agent/biomolecule complex, thereby inhibiting or delaying the onset of an immune response directed against the agent and/or agent/biomolecule complex. For example, degradation of a particle may expose both a clearance agent and an agent (and/or agent/biomolecule complex) to leukocytes. A PAMP clearance agent may allow for rapid clearance of the degraded particle by macrophages, thereby delaying an immune response (e.g., B-cell mediated immune response) against the agent and/or agent/biomolecule complex.

A clearance agent may be calreticulin, which induced phagocytosis.

In some embodiments, a particle may be cleared by an organism in about 1 day to about 5 years, such as about 1 day to about 3 years, or about 1 day to about 1 year.

VII. Methods of Administration

The disclosure contemplates that compositions described herein (e.g., any of the generally or specifically described particles or plurality of particles described herein) may be administered to cells and tissues in vitro and/or in vivo. Administration in vivo includes administration to an animal model of disease, such as an animal model of cancer, or administration to a subject in need thereof. Suitable cells, tissues, or subjects include animals, such as companion animals, livestock, zoo animals, endangered species, rare animals, non-human primates, and humans. Exemplary companion animals include dogs and cats.

For delivery in vitro, such as to and/or around cells or tissues in culture, compositions may be added to the culture media, such as to contact the microenvironment or contact soluble material in the culture media or to contact the cell or even to penetrate the cell. The desired site of activity influences the delivery mechanism and means for administering the compositions (e.g., particles described herein).

For delivery in vivo, such as to cells or tissues in vivo (including to the microenvironment of cells and tissue) and/or to a subject in need thereof, numerous methods of administration are envisioned. The particular method may be selected based on the particle composition and the particular application and the patient. Various delivery systems are known and can be used to administer agents of the disclosure. Any such methods may be used to administer any of the agents described herein. Methods of introduction can be enteral or parenteral, including but not limited to, intradermal, intramuscular, intraperitoneal, intramyocardial, intravenous, subcutaneous, pulmonary, intranasal, intraocular, epidural, and oral routes. A composition of the disclosure may be administered by any convenient route, for example, by infusion or bolus injection, by absorption through epithelial or mucocutaneous linings (e.g., oral mucosa, rectal and intestinal mucosa, etc.) and may be administered together (either concurrently or consecutively) with other biologically active agents. Administration can be systemic or local.

In certain embodiments, a composition is administered intravenously, such as by bolus inject or infusion. In certain embodiments, a composition is administered orally, subcutaneously, intramuscularly or intraperitoneally.

In certain embodiments, it may be desirable to administer a composition of the disclosure locally to the area in need of treatment (e.g., to the site of a tumor, such as by injection into the tumor).

The liver is a frequent site of metastases. Thus, in certain embodiments, delivery of an composition described herein is directed to the liver. For example, a venous catheter may be placed in the hepatic portal vein to deliver agent of the disclosure to the liver. Other methods of delivery via the hepatic portal vein are also contemplated.

In certain embodiments, compositions of the disclosure are administered by intravenous infusion. In certain embodiments, the a composition is infused over a period of at least 10, at least 15, at least 20, or at least 30 minutes. In other embodiments, the agent is infused over a period of at least 60, 90, or 120 minutes. Regardless of the infusion period, the disclosure contemplates that, in certain embodiments, each infusion is part of an overall treatment plan where agent is administered according to a regular schedule (e.g., weekly, monthly, etc.) for some period of time. However, in other embodiments, a composition is delivered by bolus injection, e.g., as part of an overall treatment plan where agent is administered according to a regular schedule for some period of time.

For any of the foregoing, it is contemplated that compositions of the disclosure (include one agent or a combination of two or more such agents) may be administered in vitro or in vivo via any suitable route or method. Compositions may be administered as part of a therapeutic regimen where a composition is administered one time or multiple times, including according to a particular schedule. Moreover, it is contemplated that the compositions of the disclosure will be formulated as appropriate for the route of administration and particular application. The disclosure contemplates any combination of the foregoing features, as well as combinations with any of the aspects and embodiments of the disclosure described herein.

The foregoing applies to any compositions (e.g., a particle or plurality of particles) of the disclosure, used alone or in combination, and used for any of the methods described herein. The disclosure specifically contemplates any combination of the features of such compositions of the disclosure, compositions, and methods with the features described for the various pharmaceutical compositions and routes of administration described in this section and below.

VIII. Pharmaceutical Compositions

In certain embodiments, the subject particle or particles of the present disclosure are formulated with a pharmaceutically acceptable carrier. One or more compositions (e.g., comprising a particle or plurality of particles described herein) can be administered alone or as a component of a pharmaceutical formulation (composition). Any of the compositions of the disclosure generally or specifically described herein may be formulated, as described herein. In certain embodiments, the composition includes two or more particles of the disclosure or a particle of the disclosure formulated with a second therapeutic agent.

A composition of the disclosure may be formulated for administration in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the subject particle or particles include, for example, those suitable for oral, nasal, topical, parenteral, rectal, and/or intravaginal administration. The formulations may conveniently be presented in unit dosage form and may be prepared by any methods well known in the art of pharmacy. The amount of active ingredient which can be combined with a carrier material to produce a single dosage form will vary depending upon the host being treated and the particular mode of administration. The amount of active ingredient which can be combined with a carrier material to produce a single dosage form will generally be that amount of the compound which produces a therapeutic effect.

In certain embodiments, methods of preparing these formulations or compositions include combining one or more particles and a carrier and, optionally, one or more accessory ingredients. In general, the formulations can be prepared with a liquid carrier, or a finely divided solid carrier, or both, and then, if necessary, shaping the product.

Formulations for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a particle of the disclosure. Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

In solid dosage forms for oral administration (capsules, tablets, pills, dragees, powders, granules, and the like), one or more compositions of the present disclosure may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like. Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

In certain embodiments, methods of the disclosure include topical administration, either to skin or to mucosal membranes such as those on the cervix and vagina. The topical formulations may further include one or more of the wide variety of agents known to be effective as skin or stratum corneum penetration enhancers. Examples of these are 2-pyrrolidone, N-methyl-2-pyrrolidone, dimethylacetamide, dimethylformamide, propylene glycol, methyl or isopropyl alcohol, dimethyl sulfoxide, and azone. Additional agents may further be included to make the formulation cosmetically acceptable. Examples of these are fats, waxes, oils, dyes, fragrances, preservatives, stabilizers, and surface active agents. Keratolytic agents such as those known in the art may also be included. Examples are salicylic acid and sulfur. Dosage forms for the topical or transdermal administration include powders, sprays, ointments, pastes, creams, lotions, gels, solutions, patches, and inhalants. The subject agents of the disclosure may be mixed under sterile conditions with a pharmaceutically acceptable carrier, and with any preservatives, buffers, or propellants which may be required. The ointments, pastes, creams and gels may contain, in addition to a subject agent of the disclosure, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to a subject agent of the disclosure, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

Pharmaceutical compositions suitable for parenteral administration may comprise one or more compositions of the disclosure in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

Injectable depot forms are made by forming microencapsule matrices of one or more particles in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

In a preferred embodiment, the compositions of the present disclosure are formulated in accordance with routine procedures as a pharmaceutical composition adapted for intravenous administration to human beings or animals, such as companion animals. Where necessary, the composition may also include a solubilizing agent and a local anesthetic such as lidocaine to ease pain at the site of the injection. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

In another embodiment, the compositions (e.g., particle or particles) described herein are formulated for subcutaneous, intraperitoneal, or intramuscular administration to human beings or animals, such as companion animals.

In certain embodiments, the agents and particles of the present disclosure are formulated for local delivery to a tumor, such as for delivery for intratumoral injection.

In certain embodiments, the composition is intended for local administration to the liver via the hepatic portal vein, and the agents and particles may be formulated accordingly.

In certain embodiments, a particular formulation is suitable for use in the context of deliver via more than one route. Thus, for example, a formulation suitable for intravenous infusion may also be suitable for delivery via the hepatic portal vein. However, in other embodiments, a formulation is suitable for use in the context of one route of delivery, but is not suitable for use in the context of a second route of delivery.

The amount of an agent or particle of the disclosure which will be effective in the treatment of a condition, such as cancer, and/or will be effective in neutralizing soluble TNFR and/or will be effective in decreasing the amount or TNF alpha binding activity of soluble TNFR, particularly soluble TNFR present in a tumor microenvironment and, optionally, in plasma and/or will be effective in inhibiting tumor cell proliferation, growth or survival in vitro or in vivo can be determined by standard clinical or laboratory techniques. In addition, in vitro assays may optionally be employed to help identify optimal dosage ranges. The precise dose to be employed in the formulation will also depend on the route of administration, and the seriousness of the condition, and should be decided according to the judgment of the practitioner and each subject's circumstances. Effective doses for administration to humans or animals may be extrapolated from dose-response curves derived from in vitro or animal model test systems.

In certain embodiments, compositions of the disclosure, including pharmaceutical preparations, are non-pyrogenic. In other words, in certain embodiments, the compositions are substantially pyrogen-free. In one embodiment the formulations of the disclosure are pyrogen-free formulations that are substantially free of endotoxins and/or related pyrogenic substances. Endotoxins include toxins that are confined inside a microorganism and are released only when the microorganisms are broken down or die. Pyrogenic substances also include fever-inducing, thermostable substances (glycoproteins) from the outer membrane of bacteria and other microorganisms. Both of these substances can cause fever, hypotension and shock if administered to humans. Due to the potential harmful effects, even low amounts of endotoxins must be removed from intravenously administered pharmaceutical drug solutions. The Food & Drug Administration ("FDA") has set an upper limit of 5 endotoxin units (EU) per dose per kilogram body weight in a single one hour period for intravenous drug applications (The United States Pharmacopeial Convention, Pharmacopeial Forum 26 (1):223 (2000)). When therapeutic proteins are administered in relatively large dosages and/or over an extended period of time (e.g., such as for the patient's entire life), even small amounts of harmful and dangerous endotoxin could be dangerous. In certain specific embodiments, the endotoxin and pyrogen levels in the composition are less than 10 EU/mg, or less than 5 EU/mg, or less than 1 EU/mg, or less than 0.1 EU/mg, or less than 0.01 EU/mg, or less than 0.001 EU/mg.

The foregoing applies to any of the agents of the disclosure, compositions, and methods described herein. The disclosure specifically contemplates any combination of the features of agents of the disclosure described herein, compositions, and methods (alone or in combination) with the features described for the various pharmaceutical compositions and routes of administration described in this section and above.

The disclosure provides numerous general and specific examples of agents and categories of agents suitable for use in the methods of the present disclosure ("agents of the disclosure"). The disclosure contemplates that any such agent or category of agent can be formulated as described herein for administration in vitro or in vivo.

Moreover, in certain embodiments, the disclosure contemplate compositions, including pharmaceutically compositions comprising any agent of the disclosure described herein formulated with one or more pharmaceutically acceptable carrier and/or excipient. Such compositions may be described using any of the functional and/or structural features of an agent of the disclosure provided herein. Any such compositions or pharmaceutical compositions can be used in vitro or in vivo in any of the methods of the disclosure.

Similarly, the disclosure contemplates an isolated or purified agent of the disclosure. An agent of the disclosure described based on any of the functional and/or structural features of an agent described herein may be provided as an isolated agent or a purified agent. Such isolated or purified agents have numerous uses in vitro or in vivo, including use in any of the in vitro or in vivo methods described herein.

IX. Applications

The compositions (e.g., particles and pharmaceutical compositions thereof) described herein are useful in a variety of diagnostic and therapeutic applications. For example, the particles described herein can be used to treat cancer, detoxify a subject, or treat viral or bacterial infection.

Therapeutic applications include administering one or more of the compositions described herein to a subject, e.g., a human subject, using a variety of methods that depend, in part, on the route of administration. The route can be, e.g., intravenous injection or infusion (IV), subcutaneous injection (SC), intraperitoneal (IP) injection, or intramuscular injection (IM).

Administration can be achieved by, e.g., local infusion, injection, or by means of an implant. The implant can be of a porous, non-porous, or gelatinous material, including membranes, such as sialastic membranes, or fibers. The implant can be configured for sustained or periodic release of the composition to the subject. See, e.g., U.S. Patent Application Publication No. 20080241223; U.S. Pat. Nos. 5,501,856; 5,164,188; 4,863,457; and 3,710,795; EP488401; and EP 430539, the disclosures of each of which are incorporated by reference in their entirety. The composition can be delivered to the subject by way of an implantable device based on, e.g., diffusive, erodible, or convective systems, e.g., osmotic pumps, biodegradable implants, electrodiffusion systems, electroosmosis systems, vapor pressure pumps, electrolytic pumps, effervescent pumps, piezoelectric pumps, erosion-based systems, or electromechanical systems.

As used herein the term "effective amount" or "therapeutically effective amount", in an in vivo setting, means a dosage sufficient to treat, inhibit, or alleviate one or more symptoms of the disorder being treated or to otherwise provide a desired pharmacologic and/or physiologic effect, e.g., modulate (e.g., enhance) an immune response to an antigen. The precise dosage will vary according to a variety of factors such as subject-dependent variables (e.g., age, immune system health, etc.), the disease, and the treatment being effected.

As used herein, a mammal can be a human, a non-human primate (e.g., monkey, baboon, or chimpanzee), a horse, a cow, a pig, a sheep, a goat, a dog, a cat, a rabbit, a guinea pig, a gerbil, a hamster, a rat, or a mouse. In some embodiments, the mammal is an infant (e.g., a human infant).

As used herein, a subject mammal "in need of prevention," "in need of treatment," or "in need thereof," refers to one, who by the judgment of an appropriate medical practitioner (e.g., a doctor, a nurse, or a nurse practitioner in the case of humans; a veterinarian in the case of non-human mammals), would reasonably benefit from a given treatment.

The term "preventing" is art-recognized, and when used in relation to a condition, is well understood in the art, and includes administration of a composition which reduces the frequency of, or delays the onset of, symptoms of a medical condition in a subject mammal relative to a subject which does not receive the composition.

Suitable human doses of any of the compositions described herein can further be evaluated in, e.g., Phase I dose escalation studies. See, e.g., van Gurp et al. (2008) *Am J Transplantation* 8(8):1711-1718; Hanouska et al. (2007) *Clin Cancer Res* 13(2, part 1):523-531; and Hetherington et al. (2006) *Antimicrobial Agents and Chemotherapy* 50(10): 3499-3500.

Toxicity and therapeutic efficacy of such compositions can be determined by known pharmaceutical procedures in cell cultures or experimental animals (e.g., animal models of cancer, toxicity, or infection). These procedures can be used, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Agents that exhibit a high therapeutic index are preferred. While compositions that exhibit toxic side effects may be used, care should be taken to design a delivery system that targets such compounds to the site of affected tissue and to minimize potential damage to normal cells and, thereby, reduce side effects.

The data obtained from the cell culture assays and animal studies can be used in formulating a range of dosage for use in humans. The dosage of such compositions lies generally within a range of circulating concentrations of the compositions that include the $ED_{50}$ with little or no toxicity. The dosage may vary within this range depending upon the dosage form employed and the route of administration utilized. A therapeutically effective dose can be estimated initially from cell culture assays. A dose can be formulated in animal models to achieve a circulating plasma concentration range that includes the $IC_{50}$ (i.e., the concentration of the antibody which achieves a half-maximal inhibition of symptoms) as determined in cell culture. Such information can be used to more accurately determine useful doses in humans.

Levels in plasma may be measured, for example, by high performance liquid chromatography. In some embodiments, e.g., where local administration is desired, cell culture or animal modeling can be used to determine a dose required to achieve a therapeutically effective concentration within the local site.

In some embodiments of any of the methods described herein, a particle can be administered to a mammal in conjunction with one or more additional therapeutic agents (e.g., therapeutic agents for treating an infection or treating cancer).

In some embodiments, the particle and additional therapeutic agent can be administered to the mammal using different routes of administration. For example, the additional therapeutic agent can be administered subcutaneously or intramuscularly and the particle can be administered intravenously.

X. Selected Applications Related to Neoplasms

In some embodiments, the particles described herein can be useful for treating a subject with cancer. Exemplary agents useful in the particle compositions described herein, and/or soluble biomolecules which can be scavenged by such particles, are described herein (e.g., Table 2) and known in the art. For example, particles capable of scavenging sTNFR, MMP2, MMP9, sIL-2R, sIL-1 receptor, and the like are useful for treating a cancer and/or for enhancing an immune response to a cancer by relieving immune dis-inhibition.

The immune dis-inhibition approach to immunotherapy is based, in part, on the concept that many cancer patients are generally immunologically competent overall but their immune systems are locally inhibited in the microenvironments of their tumors. If this inhibition of the immune system is relieved by administering a particle of the disclosure, the patient's own immune system can act on the tumor. Thus, in certain embodiments, particles of the disclosure provide an immunotherapy approach without the need for hyper-stimulating the patient's immune system by adding exogenous, active cytokines intended to bind cell surface receptors to provoke an immune response and/or without otherwise hyper-stimulating the patient's immune system.

Without being bound by theory, because the cancer patients are, generally, immunologically competent, the ability of lymphocytes to recognize tumor antigens is generally unaffected by the tumor. Thus, lymphocytes are drawn to the tumor microenvironment as they would be to any aberrant cell cluster, at which point cytokines and cytotoxic factors, such as Tumor Necrosis Factor (TNF, such as TNF alpha, the main cytotoxic "sword" of the immune system) cleave from lymphocytes into the microenvironment. If the cancer cells were instead virally infected cells, the TNF (such as TNF alpha) would engage a TNF receptor (TNFR) on the surface of the infected cell, resulting in rapid destruction by either apoptosis or oxidative stress depending on whether an R1 or R2 type receptor for TNF is engaged. In other words, in the context of a normal immune response that is not being stimulated by the presence of a tumor and/or tumor antigens, TNF deployed by lymphocytes would be available to bind cell surface TNF receptors (R1 and/or R2 receptors) as part of mounting an immune response. Even in the tumor context, the lymphocytes are deployed to the tumor site.

However, many types of cancer cells behave differently than other aberrant cell types, such as virally infected cells, in that they overproduce TNF receptors (both types) and shed them into a cloud around the tumor. Thus, the microenvironment of cancer cells and/or tumors includes amounts of soluble TNF receptors. Without being bound by theory, the soluble TNF receptor levels in the tumor microenvironment exceed that found in the microenvironment of healthy cells, such as healthy cells of the same tissue type. Additionally or alternatively, the rate and extent of TNF receptor shedding is greater for cancer cells than from healthy cells. Moreover, without being bound by theory, the levels of soluble TNF receptor found in the plasma of cancer patients may, in certain embodiments, be higher than in healthy patients.

Regardless of the mechanism, in this model, these shed, soluble TNF receptors bind to the TNF endogenously released by the recruited lymphocytes, neutralizing the endogenous TNF and effectively creating a bubble of immunologic privilege around the tumor, within which the tumor continues to grow and shed additional TNF receptors. In other words, the shed, soluble TNF receptors soak up the TNF alpha endogenously produced by lymphocytes and prevent or inhibit that TNF from binding cell surface TNF receptors on the cancer cells. This decreases or eliminates the TNF available to bind cell surface TNF receptors on the cancer cells. The soluble TNF receptors essentially outcompete for binding to TNF alpha, and thus, decrease the activity of TNF, such as TNF alpha for binding cell surface TNF receptors.

The above scenario can similarly play out in the context of IL-2 and shed, soluble IL-2 receptors.

The present disclosure provides pharmacologic approaches that can be deployed systemically or locally to relieve the inhibition of the immune system created by shed receptors in cancer (e.g., immune dis-inhibition). The present disclosure provides methods and compositions for decreasing the amount and/or activity (e.g., neutralizing the activity) of soluble TNF receptors and/or soluble IL-2 receptors (or any other soluble biomolecules that result in immune dis-inhibition) such as in the microenvironment of cancer cells and tumors. Without being bound by theory, decreasing the amount and/or activity of, for example, soluble TNF receptors (e.g., such as in the tumor microenvironment), may be used as part of a method for inhibiting proliferation, growth, or survival of a cell, such as a cancer cell. In certain embodiments, it may be used for inhibiting survival of a cell, such as a cancer cell. Exemplary methods and agents are described herein.

Regulatory T cells (TREGs) can secrete the same ligands as cancer cells as a way of tamping down the immune response to avoid, e.g., autoimmune disease caused by overactive T cells or prolonged T cell function. For instance, CD80/B7-1 and CD86/B7-2 bind to the CTLA-4 receptor on T-cells and inhibit T cell activity. Rather than blockading the CTLA-4 receptor, the particles described herein can be designed to scavenge CD80/B7-1 and/or CD86/B7-2. Likewise, the particles described herein can be designed to scavenge other immune checkpoint inhibitors, such as PD-1L, e.g., using particles comprising PD-1 receptor. Such particle compositions offer several benefits over other approaches to stimulating the immune system for the treatment of cancer.

In some embodiments, the subject is one who has, is suspected of having, or is at risk for developing a cancer. In some embodiments, the subject is one who has, is suspected of having, or is at risk for developing an autoimmune disease.

As used herein, a subject "at risk for developing" a cancer is a subject having one or more (e.g., two, three, four, five, six, seven, or eight or more) risk factors for developing a cancer. For example, a subject at risk of developing a cancer may have a predisposition to develop a cancer (i.e., a genetic predisposition to develop a cancer such as a mutation in a tumor suppressor gene (e.g., mutation in BRCA1, p53, RB, or APC) or has been exposed to conditions that can result in the condition. Thus, a subject can be one "at risk of developing a cancer when the subject has been exposed to mutagenic or carcinogenic levels of certain compounds (e.g., carcinogenic compounds in cigarette smoke such as acrolein, arsenic, benzene, benz[a]anthracene, benzo[a]pyrene, polonium-210 (Radon), urethane, or vinyl chloride). Moreover, the subject can be "at risk of developing a cancer" when the subject has been exposed to, e.g., large doses of ultraviolet light or X-irradiation, or exposed (e.g., infected) to a tumor-causing/associated virus such as papillomavirus, Epstein-Ban virus, hepatitis B virus, or human T-cell leukemia-lymphoma virus. Cancer is a class of diseases or disorders characterized by uncontrolled division of cells and the ability of these to spread, either by direct growth into adjacent tissue through invasion, or by implantation into distant sites by metastasis (where cancer cells are transported through the bloodstream or lymphatic system). Cancer can affect people at all ages, but risk tends to increase with age. Types of cancers can include, e.g., lung cancer, breast cancer, colon cancer, pancreatic cancer, renal cancer, stomach cancer, liver cancer, bone cancer, hematological cancer, neural tissue cancer (e.g., glioblastoma such as glioblastoma multiforme), melanoma, thyroid cancer, ovarian cancer, testicular cancer, prostate cancer, cervical cancer, vaginal cancer, or bladder cancer.

Similarly, a subject at risk for developing an infection is one having one or more risk factors that increase the likelihood of exposure to a pathogenic microorganism.

A subject "suspected of having" a cancer or an infection is one having one or more symptoms of the cancer or infection. It should be understood that subjects at risk for developing, or suspected of having, a cancer or an infection does not include all subjects within the species of interest.

In some embodiments, the methods include determining whether the subject has a cancer or an autoimmune disease.

XI. Selected Applications Related to Inflammatory and Autoimmune Disorders

In some embodiments, the particles described herein can be used for treating an inflammatory disorder and/or an autoimmune disorder. Exemplary agents useful in the particle compositions described herein, and/or soluble biomolecules which can be scavenged by such particles, are described herein (e.g., Table 2) and known in the art. For example, particles capable of scavenging cytokines (e.g., TNFα or interleukins, such as IL-2, IL-6, or IL-1) or chemokines (e.g., CXCL8 or CXCL1) can be useful for treating a variety of autoimmune and/or inflammatory disorders.

In some embodiments, the autoimmune or inflammatory disorder is a hypersensitivity reaction. As used herein, "hypersensitivity" refers to an undesirable immune system response. Hypersensitivity is divided into four categories. Type I hypersensitivity includes allergies (e.g., Atopy, Anaphylaxis, or Asthma). Type II hypersensitivity is cytotoxic/antibody mediated (e.g., Autoimmune hemolytic anemia, Thrombocytopenia, Erythroblastosis fetalis, or Goodpasture's syndrome). Type III is immune complex diseases (e.g., Serum sickness, Arthus reaction, or SLE). Type IV is delayed-type hypersensitivity (DTH), Cell-mediated immune memory response, and antibody-independent (e.g., Contact dermatitis, Tuberculin skin test, or Chronic transplant rejection). As used herein, "allergy" means a disorder characterized by excessive activation of mast cells and basophils by IgE. In certain instances, the excessive activation of mast cells and basophils by IgE results (either partially or fully) in an inflammatory response. In certain instances, the inflammatory response is local. In certain instances, the inflammatory response results in the narrowing of airways (i.e., bronchoconstriction). In certain instances, the inflammatory response results in inflammation of the nose (i.e., rhinitis). In certain instances, the inflammatory response is systemic (i.e., anaphylaxis).

XII. Selected Applications Related to Pathogens and Toxins

In some embodiments, the particles described herein can be designed to bind to microorganisms (e.g., viruses or bacteria) or components of microorganisms, such as endotoxin. Accordingly, the particles described herein can be useful for treat, e.g., an infectious disease (e.g., viral infectious diseases including HPV, HBV, hepatitis C Virus (HCV), retroviruses such as human immunodeficiency virus (HIV-1 and HIV-2), herpes viruses such as Epstein Barr Virus (EBV), cytomegalovirus (CMV), HSV-1 and HSV-2, and influenza virus. In addition, bacterial, fungal and other pathogenic infections are included, such as *Aspergillus, Brugia, Candida, Chlamydia, Coccidia, Cryptococcus, Dirofilaria, Gonococcus, Histoplasma, Leishmania, Mycobacterium, Mycoplasma, Paramecium, Pertussis, Plasmodium, Pneumococcus, Pneumocystis, Rickettsia, Salmonella, Shigella, Staphylococcus, Streptococcus, Toxoplasma* and Vibriocholerae. Exemplary species include *Neisseria gonorrhea, Mycobacterium tuberculosis, Candida albicans, Candida tropicalis, Trichomonas vaginalis, Haemophilus vaginalis*, Group B *Streptococcus* sp., *Microplasma hominis, Hemophilus ducreyi, Granuloma inguinale, Lymphopathia venereum, Treponema pallidum, Brucella abortus. Brucella melitensis, Brucella suis, Brucella canis, Campylobacter fetus, Campylobacter fetus intestinalis, Leptospira pomona, Listeria monocytogenes, Brucella ovis, Chlamydia psittaci, Trichomonas foetus, Toxoplasma gondii, Escherichia coli, Actinobacillus equuli, Salmonella abortus ovis, Salmonella abortus equi, Pseudomonas aeruginosa, Corynebacterium equi, Corynebacterium pyogenes, Actinobaccilus seminis, Mycoplasma bovigenitalium, Aspergillus fumigatus, Absidia ramosa, Trypanosoma equiperdum, Babesia caballi, Clostridium tetani, Clostridium botulinum*; or, a fungus, such as, e.g., *Paracoccidioides brasiliensis*; or other pathogen, e.g., *Plasmodium falciparum*. Also included are National Institute of Allergy and Infectious Diseases (NIAID) priority pathogens. These include Category A agents, such as variola major (smallpox), *Bacillus anthracis* (anthrax), *Yersinia pestis* (plague), *Clostridium botulinum* toxin (botulism), *Francisella tularensis* (tularaemia), filoviruses (Ebola hemorrhagic fever, Marburg hemorrhagic fever), arenaviruses (Lassa (Lassa fever), Junin (Argentine hemorrhagic fever), and related viruses); Category B agents, such as *Coxiella burnetti* (Q fever), *Brucella* species (brucellosis), *Burkholderia mallei* (glanders), alphaviruses (Venezuelan encephalomyelitis, eastern & western equine encephalomyelitis), ricin toxin from *Ricinus communis* (castor beans), epsilon toxin of *Clostridium perfringens; Staphylococcus* enterotoxin B, *Salmonella* species, *Shigella dysenteriae, Escherichia coli* strain O157:H7, *Vibrio cholerae, Cryptosporidium parvum*; Category C agents, such as nipah virus, hantaviruses, tickborne hemorrhagic fever viruses, tickborne encephalitis viruses, yellow fever, and multidrug-resistant tuberculosis; helminths, such as *Schistosoma* and *Taenia*; and protozoa, such as *Leishmania* (e.g., *L. mexicana*), and *Plasmodium*.

XIII. Kits for Administering the Agent

In certain embodiments, the disclosure also provides a pharmaceutical package or kit comprising one or more containers filled with at least one composition (e.g., particle or particles) of the disclosure. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

In certain embodiments, the kit includes additional materials to facilitate delivery of the subject agents. For example, the kit may include one or more of a catheter, tubing, infusion bag, syringe, and the like. In certain embodiments, a composition (e.g., comprising particles as described herein) is packaged in a lyophilized form, and the kit includes at least two containers: a container comprising the lyophilized composition and a container comprising a suitable amount of water, buffer, or other liquid suitable for reconstituting the lyophilized material.

The foregoing applies to any of the compositions and methods described herein. The disclosure specifically contemplates any combination of the features of such compositions and methods (alone or in combination) with the features described for the various kits described in this section.

These and other aspects of the present disclosure will be further appreciated upon consideration of the following Examples, which are intended to illustrate certain particular embodiments of the disclosure but are not intended to limit its scope, as defined by the claims.

EXEMPLIFICATION

Example 1—Method for Treating a Cancer

A human patient is identified by a medical practitioner as having a cancer (e.g., lung, colon, breast, brain, liver, pancreatic, skin, or hematological cancer) that shed soluble TNFR or soluble IL-2R. The patient is administered a composition comprising particles (described herein) that bind to and sequester soluble TNFR or IL-2R in an amount effective to treat the cancer. Optionally, the patient is given "maintenance doses" of the composition to maintain inhibition of the effects of soluble TNFR or IL-2R and thereby continue to enhance immune surveillance against the cancer in the patient.

Example 2—Method for Detoxifying a Human

A human patient is presents with symptoms of toxicity associated with botulinum toxin. The patient is administered a composition comprising particles (described herein) that bind to and sequester soluble botulinum toxin in an amount effective to ameliorate one or more symptoms associated with the toxicity.

Example 3—Method for Treating a Viral Infection

A human patient is identified by a medical practitioner as having an HIV-1 infection. The patient is administered a composition comprising particles (described herein) that bind to and sequester soluble HIV-1 virions in an amount effective to reduce titers of the virus in the patient's circulation. The patient is given "maintenance doses" of the composition to maintain reduction of HIV-1 virion titers and thereby suppress the infection in the patient, as well as reduce the likelihood of transmission of the virus to another.

Example 4—Method for Manufacturing Silicon Particles

Porous silicon disks are manufactured with sizes of 1000 nm by 400 nm and 1000 nm by 800 nm with variable pore sizes. The size and morphology of the disks, as well as pore diameters, are characterized by scanning electron microscopy. Gold nanoparticles (Au) are deposited in the pores of the porous silicon disks. Tumor necrosis factors (TNFs) are conjugated to the surfaces of the gold nanoparticles through dative covalent bonds. The ligand density and TNF-Au binding stabilities are assessed.

Example 5—Method for Manufacturing Polymer Particles

Poly(lactide-co-glycolide) (PLGA) particles are fabricated by emulsion. The size and morphology of the PLGA particles are characterized by scanning electron microscopy, atomic force microscopy, and transmission electron microscopy. The particles are coated with quaternary ammonium beta-cyclodextrin, for macrophage recruitment (i.e., phagocytosis). The coating is verified by atomic force microscopy and transmission electron microscopy. Coating density and uniformity is characterized by transmission electron microscopy and dynamic light scattering.

The beta-cyclodextrin-coated PLGA particles are incubated with macrophages, and phagocytosis is monitored by fluorescence microscopy and by flow cytometry.

The beta-cyclodextrin-coated PLGA particles are coated with a blend of polyethylene glycol (PEG) and thiol moieties to allow for prevention of opsonization and evasion of macrophage uptake, as well as binding to other particles. The uniformity and density of the PEG and thiol coatings are characterized by atomic force microscopy. Coating stabilities are characterized by incubating the particles in media for various periods of time. Evasion and uptake of the particles are monitored at various time points by incubating the particles with macrophages, as described above.

The PLGA particles are coated with tumor necrosis factor (TNF), and the particles are combined by disulfide bonds to form a "sponge", comprising TNF on the interior surface of the sponge. The exterior surface of the sponge is optionally blocked with particles that do not comprise TNF to prevent interactions between the TNF of the sponge and cells.

Example 6—Pharmacokinetics of Polymer-Based Particles

The sponge of Example 5 (i.e., a composition comprising "sponges" of Example 5, such as $10^3$ to $10^{12}$ sponges) is administered either intravenously or intratumorally into mouse models of primary and metastatic cancer as well as healthy controls. The toxicity of the sponge is determined by identifying $LD_{50}$'s for each route of administration. The half-life of the sponge is determined by monitoring plasma concentrations of the sponge by LC/MS and ICP for each route of administration. The biodistribution of the sponge is determined by taking biopsies of the mice and analyzing tissue for the sponge and its components by LC/MS, ICP, and confocal microscopy.

Example 7—Efficacy of Polymer-Based Particles

The sponge of Example 5 (i.e., a composition comprising "sponges" of Example 5, such as $10^3$ to $10^{12}$ sponges) is administered to mice comprising MDA-MB-231 or 4T1 xenografts. The MDA-MB-231 model is used to assess reductions in tumor size and growth, and the 4T1 model is used to assess inhibition of metastasis. The sponge is administered intratumorally to MDA-MB-231 mice once a week for 6 weeks, and body weight and tumor sizes are monitored periodically. The sponge is administered intravenously to 4T1 mice once a week for 6 weeks, and the number of metastases are monitored.

Example 8—Pharmacokinetics and Efficacy of Silicon/Gold-Based Particles

The experiments of Examples 6 and 7 are repeated with the porous silicon particles of Example 5.

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the disclosure.

What is claimed is:

1. A particle having at least one surface and an agent immobilized on the surface, wherein:
   the agent selectively binds to a target that is a first member of a specific binding pair;
   binding of the target to the particle inhibits the interaction of the target with a second member of the specific binding pair;
   the target is a soluble biomolecule;
   the soluble biomolecule is a form of a cell surface protein; and
   the agent is disposed on a surface of the particle such that it is sterically inhibited from binding or activating the cell surface protein on the surface of a cell.

2. The particle of claim 1, wherein the target is a form of a cell surface receptor protein.

3. The particle of claim 1, wherein the soluble biomolecule is a cytokine, chemokine or enzyme.

4. The particle of claim 3, wherein the cytokine, chemokine or enzyme is expressed by a cancer cell.

5. The particle of claim 1, wherein the particle is shaped and sized to circulate in the vasculature of a subject.

6. The particle of claim 5, wherein the diameter of the particle is no greater than 300 nm.

7. The particle of claim 6, wherein the diameter of the particle is no greater than 250 nm.

8. The particle of claim 5, wherein the longest dimension of the particle is no greater than about 1 µm.

9. The particle of claim 5, wherein the smallest dimension of the particle is at least about 300 nm.

10. The particle of claim 1, further comprising a coating, wherein the coating inhibits interactions between the agent and molecules on a cell surface.

11. The particle of claim 10, wherein the coating comprises a plurality of coating molecules on a surface of the particle, and the plurality of coating molecules inhibits interactions between the agent and molecules on a cell surface.

12. The particle of claim 11, wherein the plurality of coating molecules is bound to a surface of the particle.

13. The particle of claim 10, wherein:
the particle comprises an interior surface and an exterior surface;
the agent is immobilized on the interior surface and the exterior surface;
the plurality of coating molecules are bound to the exterior surface; and
the coating molecules inhibit interactions between the agent and molecules on a cell surface.

14. The particle of claim 10, wherein the coating increases the clearance of the particle in vivo.

15. The particle of claim 14, wherein the coating increases the clearance of the particle by phagocytosis, renal clearance, or hepatobiliary clearance.

16. The particle of claim 10, wherein the coating decreases the clearance of the particle in vivo.

17. The particle of claim 10, wherein the coating is biodegradable.

18. The particle of claim 17, wherein the coating comprises a biodegradable polymer.

19. The particle of claim 1, wherein the agent is a ligand of a cell surface receptor protein.

20. The particle of claim 19, wherein the agent is a natural ligand of a cell surface receptor protein.

21. The particle of claim 1, wherein the cell surface receptor protein, when activated on a cell surface, induces apoptosis.

22. The particle of claim 1, wherein the surface is oriented such that the agent has a reduced ability to bind to a molecule on the surface of a cell.

23. The particle of claim 1, wherein the agent has a reduced ability to activate a cell surface receptor protein, relative to the ability of a natural ligand of the cell surface receptor protein.

24. The particle of claim 23, wherein the agent does not activate the cell surface receptor protein.

25. The particle of claim 1, wherein the agent is a small molecule, a macrocycle compound, a polypeptide, a protein, a peptide, a peptidomimetic compound, a nucleic acid, or a nucleic acid analog.

* * * * *